United States Patent
Townsend et al.

(10) Patent No.: US 7,517,680 B2
(45) Date of Patent: Apr. 14, 2009

(54) **PRODUCTION OF CLAVULANIC ACID BY GENETIC ENGINEERING OF *STREPTOMYCES CLAVULIGERUS***

(75) Inventors: Craig A. Townsend, Baltimore, MD (US); Rong-feng Li, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/530,118

(22) Filed: Sep. 8, 2006

(65) Prior Publication Data

US 2007/0161092 A1 Jul. 12, 2007

Related U.S. Application Data

(60) Provisional application No. 60/715,999, filed on Sep. 9, 2005.

(51) Int. Cl.
*C12N 1/21* (2006.01)
*C12P 17/00* (2006.01)
*C07H 21/04* (2006.01)

(52) U.S. Cl. ............................. 435/252.35; 536/23.2

(58) Field of Classification Search ........................ None
See application file for complete search history.

(56) References Cited

OTHER PUBLICATIONS

Sprusansky et al. 2001 Microbiol 2001, 147, 1291-1301.*
Growth limiting substrate affects antibiotic production and associated metabolic fluxes in streptomyces clavuligerus, Kirk et al.(Biotech lett. 2000, 22, pp. 1803-1800).*
Gap1 glyceraldehyde 3-phosphate dehydrogenase ( streptomyces avermitliis MA-4680, Bentley et al. ( ncbi GENBANK gene ID 1097381).*
Homo fermentative production of D or L-Lactate in metabolically engineered *Escherichia coli* RR1, Chang et al. Appld and envrn Microbiol 1999, pp. 1384-1389.*

* cited by examiner

*Primary Examiner*—Nashaat T Nashed
*Assistant Examiner*—MD. Younus Meah
(74) *Attorney, Agent, or Firm*—Whitham, Curtis, Christofferson & Cook, PC

(57) ABSTRACT

Genetically engineered *Streptomyces clavuligerus* strains with improved capabilities to produce clavulanic acid are provided. The strains are genetically engineered by disrupting newly identified glyceraldehyde-3-phosphate dehydrogenase (GAPDH) genes. This results in an increased intracelluar pool of the clavulanic acid precursor D-glyceraldehyde-3-phosphate (D-G3P), and increased clavulanic acid production. Clavulanic acid production may be further increased by supplying arginine to the medium in which the *S. clavuligerus* is grown.

2 Claims, 15 Drawing Sheets

|  | (Motif M1)<br>Gap-Deg-5 →  |  | (Motif M2)<br>Gap-Deg-5-2 →  |  | (Motif M3)<br>Gap-Deg-3 →  |  |
|---|---|---|---|---|---|---|
| S. coelicolor | 145 HHVISNASCTTN (SEQ ID NO:1) | .37. | KDLRRARAAA (SEQ ID NO:2) | .120. | WYDNEWGYSN (SEQ ID NO:3) | 323 |
| T. tengcongensis | 145 HHVISNASCTTN (SEQ ID NO:4) | .37. | SDLRRARAAA (SEQ ID NO:5) | .109. | WYDNEWGYSN (SEQ ID NO:6) | 322 |
| T. fusca | 146 HHILSNASCTTN (SEQ ID NO:7) | .37. | KDLRRARAAA (SEQ ID NO:8) | .108. | WYDNEWGYSN (SEQ ID NO:9) | 322 |
| S. aureofacien | 144 HTIVSNASCTTN (SEQ ID NO:10) | .37. | RDPRRARAAA (SEQ ID NO:11) | .108. | WYDNEWGFSN (SEQ ID NO:12) | 320 |
| M. tuberculosis | 151 QNIISNASCTTN (SEQ ID NO:13) | .37. | KDLRRARAAA (SEQ ID NO:14) | .108. | WYDNEWGYSN (SEQ ID NO:15) | 326 |
| B. megaterium | 144 HNVISNASCTTN (SEQ ID NO:16) | .37. | KDYRRARAAA (SEQ ID NO:17) | .109. | WYDNESGYSN (SEQ ID NO:18) | 321 |
| M. avium | 151 QNIISNASCTTN (SEQ ID NO:19) | .37. | KDLRRARAAA (SEQ ID NO:20) | .108. | WYDNEWGYSN (SEQ ID NO:21) | 326 |
| S. arenae | 145 HTIISNASCTTN (SEQ ID NO:22) | .37. | KDLRRARAAA (SEQ ID NO:23) | .107. | WYDNEWGYSN (SEQ ID NO:24) | 320 |
| O. iheyensis | 144 HNVISNASCTTN (SEQ ID NO:25) | .37. | KDYRRARAAA (SEQ ID NO:26) | .109. | WYDNEWGYSA (SEQ ID NO:27) | 321 |
| S. avermitilis | 145 HNVISNASCTTN (SEQ ID NO:28) | .37. | KDLRRARAAA (SEQ ID NO:29) | .109. | WYDNEWGYSN (SEQ ID NO:30) | 322 |
| C. tetani | 145 HNIISNASCTTN (SEQ ID NO:31) | .37. | KDLRRARAAA (SEQ ID NO:32) | .109. | WYDNEWGYST (SEQ ID NO:33) | 322 |
| B. cereus | 137 HNVVSNASCTTN<br>..:********<br>(SEQ ID NO:34) | .37. | KDLRRARAAA<br>* *****<br>(SEQ ID NO:35) | .109. | WYDNETGYSN<br>*** * . *<br>(SEQ ID NO:36) | 314 |

*Figure 2A*

```
Gap-Deg-5:    5'- ATC ATC TCC AAC GCC TCC tgy acn acn aa -3' (SEQ ID NO:37)
                   I   I   S   N   A   S   C   T   T        (SEQ ID NO:38)

Gap-Deg-5-2:  5'- GAC CTC CGC CGC GCC mgn gcn gcn gc -3'    (SEQ ID NO:39)
                   D   L   R   R   A   R   A   A            (SEQ ID NO:40)

Gap-Deg-3:    5'- T GGA GTA GCC CCA CTC gtt rtc rta cca -3' (SEQ ID NO:41)
                    S   Y   G   W   E   N   D   Y   W       (SEQ ID NO:42)
```

GTGACGATCCGCGTAGGCATCAACGGCTTTGGCCGCATCGGTCGTAACTACTT
CCGCGCTGCTGGAGCAGGGTGCAGACATCGAGATCGTGGCTGTCAACGAC
CTGGGTGACACCGGCACCGGGTCACCTGCTGAAGTACGACACCATTCTGG
GACGCCTCAAGGCCGAGGTCACCACACCGCGACACCATCACCGTCGACGG
CCACACGATCAAGGTGCTCTCCGAGCGCAACCCCGCGACATCCGTGGGGC
GAGCTGGGCGTCGACATCGTGATCGAGTCGACGGGCATCTTCACCAAGAAGG
CCGACGCCGAGAAGCACCTCGCCGGCGCCAAGAAGGTCCTGATCTCGGC
TCCGGCCAAGGACGAGGACATCACCCCTGGTGATGGGTGTCAACGGACACC
TACGACCCGGGCCAGCACCGTCATCTCCAAGCCTCCTGCACCACCAACT
GTGTGGCGCCGATGGCGAAGGTGCTCGACGAGAACTTCGGCATCGTCCGCG
TCTGATGACGACGGTCCACGCCTACACCAAGCGACCAGCCATCCTGGACTTC
CCGCACTCGGACCTGCAAGGCCGCGGAGAACATCATCCCGA
CCACCACGGGTGCCGCCAAGGCCATGCCGCCACCGGCCCTGTCCCCCGACC
CAAGCTGGACGGCATCGCCAGGGCCGAGGTCACCAAGGACGAGGTCAAGCC
GACCTGTCGTGAGCTGTGAGCCGGAGTCCAGGCATCCTGAGTCGTACACCG
GCGTTCAAGAAGGCCGAGACCCGGGACCCTCTGCACCTTC
AGGACCCGATCGTCTCCGGACATCGTGGCCAACTGGCTGTGAAGATCCGGCT
GACTCCCCTGACCATGGTCCAGGAGGGCAACTGGGTGAAGATCCTCGGCT
GGTACGACAACGAGTGGGCTACTCCAACCGCCTCGTCGACCTCACGGTCTT
CGTCGGGGCGAGCAGCTCTGA

*Figure 3B*

```
GTGACTGTCAATGAGGACTCGTTCACCAACTGGAAGAACCGCGAGGAGATCG
CGGAGTCGATGATCCCGGTCATCGGCAAGCTCCACCGGGAGCGGGACGTCAC
GATCCTGCTCCACAGCCGTCCCTGGTGAACAAGTCGGTGTCAGCATCCTCA
AGACCCACCGTTCGCTCGCCAGATCGCCGGCGAGGAGCTGTCCGTCACCGA
GACGCTGCCCTTCCTCAAGACCCTGCGACCCTGGATCTCGCCCCTCCCAGA
TCGACCTGGGCATGCTCGCCGCGACCTACCGGGACGACCGCGGGTCTGAC
GGTGGAGGAGTTCACCGCGGAGGCCGTGCGCCGGGTGCCACGGGTGCCAACAA
GATCGAGGCGGCGAGGGACGCGATGTCGTCCTCTACGGGTTCGCGCCGCATC
GGCCGTCTCCTCGCCGCCATCGTCGTCCGCAAGAAGGCCGGCTCCGGCAACGGC
TGCGCCTGCGCCGCCATCGTCGTCCGCAAGGGCGGGGCCAGGACCTCGTCAA
GCGCGCCTGCTGCTCCGTGCTGCTCCAGGCCAGTTCCACGGCACG
ATCACCGTGGACGAGGAGAACAGCACCATCGTCGCAACGGCAACGAGATC
AAGGTGATCTACTGGACGGTGGACGGTGACTACACCGCGTACGGCA
TCGGGACGCCATCCTCATCGACACAACACCGGCCGCTGGGCGACCGCGAGGG
CCTGTCGAAGCATCTGCGCCCCGGTATCGCCAAGGTGGTCCTGACCGCCCCG
GGCAAGGCGACGTCCCCAACATCGTCAAGCGGCCTCCTGCACCACGATCA
AGCCGGACGAGCAGATCCTGTCCTGCCGTCCTGCACCACCAACGCGATCGT
CCCGCCGCTGAAGGCGATGGGGACGAGTTCGGTGTCCTCGGGGGCCATGTG
GAGACGGTCCACTCGTACACGAACGCCGCTCGGACAACCTGCTGACAACTACCACA
AGTCCGACCGCCGCTGCGACCTCGCTCGGCCGCTCAATATGGTGATCACCGAGAC
CGGTGCCGCCTCCGCCGGTGCCGGGCCAAGGGCGCTGCCGACCTCAAGGCGAAGATC
ACCGGAAGCTCCATCCGGGTGCCGGAGACCACCCGGATGTCTCGATCGCGATCCTCA
GCCTGCGGCTCGGGCGAGAAGGTGAGGACCGGAAGTCCTGACCATCTGCG
TGAGGTGTCGCTGACCTCGCCGCGCTCAAGCCCAGATCGACTTCATCACGGCG
CCCGACGCGGTGTCGAACGACTTCGTCGGCCTCCGGCCACGCCTCCATCGTGG
ACGCCGGAGCCACCAAGGTCGAGGGCGACAACGCGATCCTGTACCTGTGGTA
CGACAACGAGTTCGGCTACTCTCGCCAGTGCGTCGCCGGTGGTCCAGCACGTC
TCCGGGTGAGTACCCGACCTTCCCGGCCGGTCGCCTGA
```

*Figure 3C*

MTVNEDSFTNWKNREEIAESMIPVIGKLHRERDVTILLHSRSLVNKSVVSILKTHR
FARQIAGEELSVTETLPFLKTLAALDLGPSQIDLGMLAATYRADDRGLTVEEFTA
EAVAGATGANKIERREGRDVVLYGFGRIGRLLARLLIEKAGSGNGLRLRAIVVRK
GAGQDLVKRASLLRDSIHGQFHGTITVDEENSTIVANGNEIKVIYSDDPTAVDY
TAYGIRDAILIDNTGRWRDREGLSKHLRPGIAKVVLTAPGKGDVPNIVHGVNHD
TIKPDEQILSCASCTTNAIVPPLKAMADEFGVLGGHVETVHSYTNDQNLLDNYHK
SDRRGRSAALNMVITETGAASASAVAKALPDLKAKITGSSIRVPVPDVSIAILSRLG
RETTREEVLDHLREVSLTSPLKRQIDFITAPDAVSNDFVGSRHASIVDAGATKVEG
DNAILYLWYDNEFGYSCQVVRVVQHVSGVEYPTFPAPVA*

*Figure 3D*

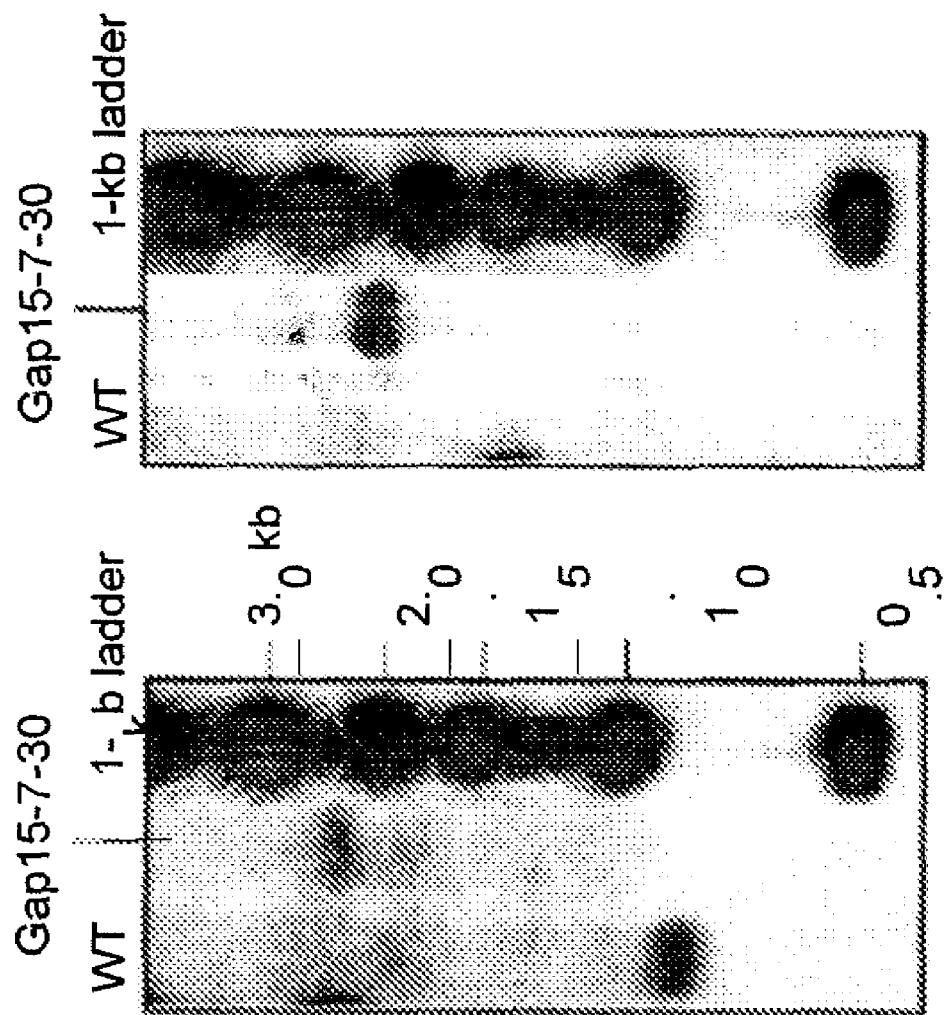

tccccgcggtggcggccgctctagaactagtggatccccattcatctccaacgcctcctgtaccaccaactgtgtggcgccgatggcgaag
gtgctcgacgagaacttcggcatcgtccgcggtctga<ins>ATGACGACGGTCCACGCCTACACCAACGACCA
GCGCATCCTGGACTTCCCGCACTCGGACCTGCGCCGCGCCCGCGCCGCCGCGG
AGAACATCATCCCGACCACCACGGGTGCCGCCAAGGCCACCGCGCTGGTCCTC
CCGCAGCTCAAGGGCAAGCTGGACGGCATCGCCATGCGCGTCCCGGTCCCCAC
CGGCTCCGCGACCGACCTGGTCGTCGAGCTGWGATCAAGGCGAATACTTCATATG
SGGGGATCGACCGCGCGGGTCCCGGACGGGGAAGAGCGGGGAGCTTTGCCAGAGAG
CGACGACTTCCCCTTGCGTTGGTGATTGCCGGTCAGGGCAGCCATCCGCCATCGTCG
CSTAGGGTGTCACACCCCAGGAATCGCGTCACTGAACACAGCAGCCGGTAGGACGAC
CATGACTGAGTTGGACACCATCGCAAATCCGTCCGATCCCGCGGTGCAGCGGATCAT
CGATGTCACCAAGCCGTSGCGATCCAACATAAAGACAACGTTGATCGAGGACGTCGA
GCCCCTCATGCACAGCATCGCGGCCGGGGTGGAGTTCATCGAGGTCTACGGCAGCGA
CAGCAGTCCTTTTCCATCTGAGTTGCTGGATCTGTGCGGGCGGCAGAACATACCGGT
CCGCCTCATCGACTCCTCGATCGTCAACCAGTTGTTCAAGGGGGAGCGGAAGGSCAA
GACATTCGGCATCGCCCGCGTCCCTCGCCCGGCCAGGTTCGGCGATATCGCGAGCCG
GCGTGGGGACGTCGTCGTTCTCGACGGGGTGAAGATCGTCGGGAACATCGGCGCGAT
AGTACGCACGTCGCTCGCGCTCGGAGCGTCGGGGATCATCCTGGTCGACAGTGACAT
CACCAGCATCGCGGACCGGCGTCTCCAAAGGGCCAGCCGAGGTTACGTCTTCTCCCT
TCCCGTCGTTCTCTCCGSTCGCGAGGAGGCCATCGCCTTCATTCGGGACAGCGGTATG
CAGCTGATGACGCTCAAGGCGGATGGCGACATTTCCGTGAAGGAACTCGGGGACAA
TCCGGATCGGCTGGCCTTGCTGTTCGGCAGCGAAAAGGGTGGGCCTTCCGACCTGTT
CGAGGAGGCGTCTTCCGCCTCGGTTTCCATCCCCATGATGAGCCAGACCGAGTCTCT
CAACGTTTCCGTTTCCCTCGGAATCGCGCTGCACGAGAGGATCGACAGGAATCTCGC
GGCCAACCGATAAGCGCCTCTGTTCCTCGGACGCTCGGTTCCTCGACCTCGATTCGTC
AGTGATGATC<ins>TGAGCCGCGAGGTCACCAAGGACGAGGTCAACGCCGCGTTCAAG
AAGGCCGCCGAGGGCGAGCTCCAGGGCATCCTGAGCTACACCGAGGACCCGAT
CGTCTCCTCGGACATCGTCGGCGACCCGGCCTCCTGCACCTTCGACTCCTCCCT
GACCATGGTCCAGGAGGGCAACTCGGTGAAGATCCTCGGCTGGTATGAAACGA
GTGGGGCTACTCCA</ins>gggctgcaggaattcgatatcaagcttatcgataccgtcgacctcgaggagggc

Figure 6

GTGACTGTCAATGAGGACTCGTTCACCAACTGGAAGAACCGCGAGGAGA
TCGCGGAGTCGATGATCCCGGTCATCGGCAAGCTCCACCGGGAGCGGG
ACGTCACGATCCTGCTCCACAGCCGTTCCCTGGTGAACAAGTCGGTGGT
CAGCATCCTCAAGACCCACCGTTTCGCTCGCCAGATCGCCGGCGAGGAG
CTGTCCGTCACCGAGACGCTGCCCTTCCTCAAGACCCTCGCCGCCCTGG
ATCTCGGCCCCTCCCAGATCGACCTGGGCATGCTCGCCGCGACCTACCG
GGCGGACGACCGCGGTCTGACGGTGGAGGAGTTCACCGCCGAGGCCGT
CGCCGGTGCCACGGGTGCCAACAAGATCGAGCGCCGCGAGGGACGCGA
TGTCGTCCTCTACGGGTTCGGCCGCATCGGCCGTCTCCTCGCCCGCCTG
CTCATCGAGAAGGCCGGCTCCGGCAACGGGCTGCGCCTGCGCGCCATC
GTCGTCCGCAAGGGCGCGGGCCAGGACCTCGTCAAGCGCGCCTCGCTG
CTCCGCCGTGACTCGATCCACGGCCAGTTCCACGGCACGATCACCGTGG
ACGAGGAGAACAGCACCATCGTCGCCAACGGCAACGAGATCAAGGTGAT
CTACTCGGACGACCCGACGGCGGTGGACTACACCGCGTACGGCATCCGG
GACGCCATCCTCATCGACAACACCGGCCGCTGGCGCGACCGCGAGGGC
CTGTCGAAGCATCTGCGCCCCGGTATCGCCAAGGTGGTCCTGACCGCCC
CGGGCAAGGGCGACGTCCCCAACATCGTCCACGGCGTCAACCACGACAC
GATCAAGCCGGACGAGCAGATCCTGTCCTGCGCCTCCTGCACCACCAAC
GCGATCGTCCCGCCGCTGAAGGCGATGGCGGACGAGTTCGGTGTCCTCG
GCGGCCATGTGGAGACGGTCCACTCGTACACGAACGACCAGAACCTGCT
GGACAACTACCACAAGTCCGACCGCCGTGGCCGCTCGGCCGCGCTCAAT
ATGGTGATCACCGAGACCGGTGCCGCCTCCGCCGTGGCCAAGGCGCTGC
CCGACCTCAAGGCGAAGATCACCGGAAGCTCCATCCGGGTGCCGGTGCC
GGATGTCTCGATCGAATTCAGATGCTCACGGTAACTGATGCCGTATTTGCAG
TACCAGCGTACGGCCCACAGAATGATGTCACGCTGAAAATGCCGGCCTTTGA
ATGGGTTCATGTGCAGCTCCATCAGCAAAAGGGGATGATAAGTTTATCACCA
CCGACTATTTGCAACAGTGCCGTTGATCGTGCTATGATCGACTGATGTCATCA
GCGGTGGAGTGCAATGTCGTGCAATACGAATGGCGAAAAGCCGAGCTCATCG
GTCAGCTTCTCAACCTTGGGGTTACCCCCGGCGGTGTGCTGCTGGTCCACAGC
TCCTTCCGTAGCGTCCGGCCCCTCGAAGATGGGCCACTTGGACTGATCGAGG
CCCTGCGTGCTGCGCTGGGTCCGGGAGGGACGCTCGTCATGCCCTCGTGGTC
AGGTCTGGACGACGAGCCGTTCGATCCTGCCACGTCGCCCGTTACACCGGAC
CTTGGAGTTGTCTCTGACACATTCTGGCGCCTGCCAAATGTAAAGCGCAGCGC
CCATCCATTTGCCTTTGCGGCAGCGGGGCCACAGGCAGAGCAGATCATCTCT
GATCCATTGCCCCTGCCACCTCACTCGCCTGCAAGCCCGGTCGCCCGTGTCCA
TGAACTCGATGGGCAGGTACTTCTCCTCGGCGTGGGACACGATGCCAACACG
ACGCTGCATCTTGCCGAGTTGATGGCAAAGGTTCCCTATGGGGTGCCGAGAC
ACTGCACCATTCTTCAGGATGGCAAGTTGGTACGCGTCGATTATCTCGAGAAT
GACCACTGCTGTGAGCGCTTTGCCTTGGCGGACAGGTGGCTCAAGGAGAAGA
GCCTTCAGAAGGAAGGTCCAGTCGGTCATGCCTTTGCTCGGTTGATCCGCTCC
CGCGACATTGTGGCGACAGCCCTGGGTCAACTGGGCCGAGATCCGTTGATCT
TCCTGCATCCGCCAGAGGCGGGATGCGAAGAATGCGATGCCGCTCGCCAGTC
GATTGGCTGAGCTCATGAGCGGAGAACGAGATGACGTTGGAGGGGCAAGGT
CGCGCTGATTGCTGGGGCAACACGTGGAGCGGATCGGGGATTGTCTTTCTTC
AGCTCGCTGATGATATGCTGACGCTCAATGCCGTTTGGCCTCCGACTAACGAA
AATCCCGCATTTGGACGGCTGATCCGATTGGCACGGCGGACGGCGAATGGCG

*Figure 7A*

GAGCAGACGCTCGTCCGGGGGCAATGAGATATGAAAAAGCCTGAACTCACC
GCGACGTCTGTCGAGAAGTTTCTGATCGAAAAGTTCGACAGCGTCTCCGACC
TGATGCAGCTCTCGGAGGGCGAAGAATCTCGTGCTTTCAGCTTCGATGTAGG
AGGGCGTGGATATGTCCTGCGGGTAAATAGCTGCGCCGATGGTTTCTACAAA
GATCGTTATGTTTATCGGCACTTTGCATCGGCCGCGCTCCCGATTCCGGAAGT
GCTTGACATTGGGGAATTATCACGAAT<u>TCGATCCTCAGCCTGCGGCTCGGG</u>
<u>CGCGAGACCACCCGTGAGGAAGTCCTCGACCATCTGCGTGAGGTGTCGC</u>
<u>TGACCTCGCCGCTCAAGCGCCAGATCGACTTCATCACGGCGCCCGACGC</u>
<u>GGTGTCGAACGACTTCGTCGGCTCGCGCCACGCCTCCATCGTGGACGCC</u>
<u>GGAGCCACCAAGGTCGAGGGCGACAACGCGATCCTGTACCTGTGGTACG</u>
<u>ACAACGAGTTCGGCTACTCCTGCCAGGTCGTCCGCGTGGTCCAGCACGT</u>
<u>CTCCGGGGTGGAGTACCCGACCTTCCCGGCGCCGGTCGCCTGA</u>

PRODUCTION OF CLAVULANIC ACID BY GENETIC ENGINEERING OF *STREPTOMYCES CLAVULIGERUS*

CROSS-REFERENCE TO RELATED APPLICATIONS

This application claims benefit of U.S. provisional patent application 60/715,999, filed Sep. 9, 2005, the complete contents of which are hereby incorporated by reference.

BACKGROUND OF THE INVENTION

1. Field of the Invention

The invention generally relates to the improvement of clavulanic acid production in *Streptomyces clavuligerus* by genetic engineering. In particular, the invention provides genetically engineered *S. clavuligerus* in which a newly identified glyceraldehyde-3-phosphate dehydrogenase (GAPDH) gene is disrupted, resulting in increased clavulanic acid production.

2. Background of the Invention

The β-lactams penicillin and cephalosporin were among the first useful antibiotics discovered and remain at the forefront of clinical use to combat bacterial infections. The widespread use of β-lactam antibiotics for more than 50 years, however, has reduced their effectiveness owing to the emergence of resistance among invading pathogens. As a consequence, strategies aimed at overcoming acquired resistance have become of increasing interest. One of the best examples in broad clinical application is the development of β-lactamase inhibitors. The discovery of clavulanic acid was reported in 1976, (Reading and Cole, 1977) and it has been shown to be a potent inhibitor of β-lactamases produced by staphylococci and plasmid-mediated β-lactamases of *E. coli*, as well as species from *Klebsiella*, *Proteus*, and *Hemophilus* (Brown et al., 1976). The molecule is produced by the filamentous bacterium *Streptomyces clavuligerus*, and consists of a β-lactam ring fused to an oxazolidine ring (Howarth et al., 1976; Reading and Cole, 1977). Commercial products such as Augmentin® and Timentin®, which are combinations of clavulanic acid and other established β-lactam antibiotics, are prescribed in more than 150 countries and have attained sales in excess of 2 billion dollars yearly (Elander, 2003).

To date strain improvement of microorganisms to obtain high-titers of secondary metabolites that are more suitable for industrial fermentations has depended largely on random mutagenesis and selection techniques. However, development of a new generation of high production strains with this approach often takes 5 years or more (Nielsen, 1997). A significant drawback is the introduction of a limited spectrum of base-pair substitutions that do not readily solve the specific rate limitations of biosynthetic pathways (Baltz, 1998). In the past few years, as techniques for molecular genetics have become increasingly sophisticated, the ability to modify existing pathways or create non-native pathways has advanced rapidly. Progress in genetics, transcriptional analysis, proteomics, metabolic reconstructions and metabolic flux analysis offer genetic engineering as an alternative approach for strain improvement in a targeted manner (Baltz, 2001). Duplication of specific genes thought to be involved in rate limiting steps can be achieved by inserting the desired gene(s) into a chromosome by homologous recombination or by site-specific integration. In *S. clavuligerus*, gene dosage constructs of the biosynthetic genes ceas and cs2 resulted in recombinant strains with 60% and 100% higher clavulanic acid production, respectively, compared to the wild-type strain (Perez-Redondo et al., 1999). Disruption of negative regulatory gene(s), or increased expression of positive regulatory gene(s) also can result in the elevated production of secondary metabolites. Paradkar, et al. observed a 2 to 3-fold increase in clavulanic acid production by introducing additional copies of positive regulatory genes in the wild-type (Paradkar et al., 1998; Perez-Llarena et al., 1997; Perez-Redondo et al., 1998). A third approach is to inactivate pathways that compete for key precursors, intermediates, cofactors and energy supply. The inactivation of the clavam pathway, which shares the common intermediate clavaminic acid with the clavulanic acid pathway, has been shown to give an elevated yield of clavulanic acid in *S. clavuligerus* (Paradkar et al., 2001).

The primary metabolic precursors of clavulanic acid are D-glyceraldehyde-3-phosphate (G3P) (Khaleeli et al., 1999) and L-arginine (Valentine et al., 1993). The observation of arginase and ornithine carbamoyltransferase activities are strongly suggestive of a functional urea cycle in *S. clavuligerus* (Bascaran et al., 1989; Ives and Bushell, 1997; Romero et al., 1986). The prokaryotic urea cycle is unusual and provides a very effective pathway for arginine biosynthesis such that the pool size of this amino acid could remain sufficient to support an increased rate of clavulanic acid production. Supplemented fermentations of *S. clavuligerus* with arginine increases only the intracellular pool size of this precursor, but not the production of clavulanic acid (Chen et al., 2002; Chen et al., 2003). Metabolic flux analysis has further suggested that a limiting factor for clavulanic acid biosynthesis is the $C_3$ precursor, G3P (Ives and Bushell, 1997). This deduction was supported by the observation of a stimulatory effect on clavulanic acid production by supplementing cultures of *S. clavuligerus* with glycerol (Chen et al., 2003). G3P is an intermediate of the glycolytic pathway and also the entry point in the gluconeogenesis pathway for the synthesis of glucose. Metabolic analysis has further shown that in wild-type *S. clavuligerus* the favored direction of G3P flux (~80%) is consistently towards the glycolytic pathway, and the rest (~20%) enters the gluconeogenesis and clavulanic acid pathways (Kirk et al., 2000) (see FIG. 1). G3P is converted into 1,3-bisphosphoglycerate by glyceraldehyde-3-phosphate dehydrogenase (GAPDH) in the glycolytic pathway and finally enters the Krebs cycle through pyruvate.

While these observations suggest that increasing the intracellular pool of G3P could result in enhanced clavulanic acid production in *S. clavuligerus*, the prior art has thus far failed to exploit this potential, even though there is an ongoing need to develop additional strains with improved capacity to produce high yields of clavulanic acid.

SUMMARY OF THE INVENTION

The present invention is based on the identification of a new *S. clavuligerus* glyceraldehyde-3-phosphate dehydrogenase gene (gap1), and on the discovery that disruption of gap1 by genetic engineering results in *S. clavuligerus* mutants in which clavulanic acid production is significantly elevated. Without being bound by theory, it appears that, in gap1 disruption mutants, the $C_3$ pool available for clavulanic acid synthesis is increased dramatically, likely by diversion of the $C_3$ flux away from the glycolytic pathway, which requires a functional GAPDH activity. The $C_3$ pool increases to such an extent that L-arginine becomes the rate-limiting precursor for clavulanic acid biosynthesis. Thus, in a fed-batch culture of the *S. clavuligerus* gap1 mutants of the invention, a further improvement in clavulanic acid production is observed when the media is supplemented with arginine.

The invention provides *Streptomyces clavuligerus* genetically modified such that at least one sequence encoding glyceraldehyde-3-phosphate dehydrogenase (GAPDH) activity is missing, not functioning, or functioning at a reduced rate, or progeny thereof.

The invention further provides a *Streptomyces* genetically modified such that at least one sequence encoding glyceraldehyde-3-phosphate dehydrogenase (GAPDH) activity is missing, not functioning, or functioning at a reduced rate, or progeny thereof.

The invention further provides a host cell genetically modified such that at least one sequence encoding glyceraldehyde-3-phosphate dehydrogenase (GAPDH) activity is missing, not functioning, or functioning at a reduced rate, or progeny thereof.

The invention also provides a method for producing clavulanic acid. The method comprises the steps of 1) growing *Streptomyces clavuligerus* genetically modified such that at least one sequence encoding glyceraldehyde-3-phosphate dehydrogenase (GAPDH) activity is missing, not functioning, or functioning at a reduced rate, or progeny thereof; and 2) recovering clavulanic acid produced by said genetically modified *S. clavuligerus* or progeny thereof. In some embodiments, the step of growing includes providing arginine.

The invention further provides a method for producing clavulanic acid. The method comprises the steps of 1) growing to *Streptomyces* genetically modified such that at least one sequence encoding glyceraldehyde-3-phosphate dehydrogenase (GAPDH) activity is missing, not functioning, or functioning at a reduced rate, or progeny thereof; and 2) recovering clavulanic acid produced by said genetically modified *S. clavuligerus*, or progeny thereof. In some embodiments, the step of growing includes providing arginine.

The invention further provides a method for producing clavulanic acid that comprises the steps of 1) growing a host cell genetically modified such that at least one sequence encoding glyceraldehyde-3-phosphate dehydrogenase (GAPDH) activity is missing, not functioning, or functioning at a reduced rate, or progeny thereof; and 2) recovering clavulanic acid produced by said genetically modified *S. clavuligerus*, or progeny thereof. In some embodiments, the step of growing includes providing arginine.

The invention also provides a gap1 gene, a Gap1 protein, a gap2 gene, and a Gap2 protein. Further, a DNA sequence as represented by SEQ ID NO: 50; an amino acid sequence as represented by SEQ ID NO: 43; a DNA sequence as represented by SEQ ID NO: 53; and an amino acid sequence as represented by SEQ ID NO: 56 are also provided.

The invention further provides a process of: 1) impeding a primary metabolic pathway by genetically modifying a host cell such that at least one DNA sequence coding for at least one activity in said primary metabolic pathway is missing, not functioning, or functioning at a reduced rate, or encodes a gene product that is not functioning, or functioning at a reduced rate, said impeding step producing a genetically modified host cell; and 2) providing nutrients to said genetically modified host cell or progeny thereof, whereby said impeding step increases production of one or more chemical species in one or more secondary pathways. In one embodiment of the invention, the primary metabolic pathway is the glycolytic pathway. In one embodiment of the invention, the secondary pathway is a clavulanic acid biosynthetic pathway. In yet another embodiment of the invention, the secondary pathway is a non-mevalonate biosynthetic pathway. In some embodiments of the invention, the impeding step eliminates, prevents the function of, or causes functioning at a reduced rate of Gap1. In other embodiments, the impeding and providing steps are performed in a host cell which is a plant cell. In yet other embodiments, the impeding and providing steps are performed in a host cell which is a *Streptomyces*.

The invention further provides a diagnostic for identifying the presence or absence of gap1 or gap2, or both, in a host.

The invention thus provides, in a host cell, a process of impeding at least a portion of a "primary" metabolic pathway (i.e., a pathway considered essential for life such as the glycolytic pathway, Krebs cycle, etc.) to benefit a "secondary" pathway (i.e., a pathway not considered essential for life such as the pathway for clavulanic acid production and the non-mevalonate pathway) while maintaining the viability (and preferably normal functioning) of the host cell. For example, the glycolytic pathway in a host cell can be impeded by genetically modifying said host to either lack at least one gene coding for GADPH activity, or to have a non-functioning or reduced functioning gene, or to encode a non-functioning or reduced functioning gene product. The host cell can be provided with nutrients (e.g., glycerol, arginine, ornithine, vitamins, proteins, carbohydrates, lipids, etc.) that might otherwise be used in the "primary" metabolic pathway. Having the primary pathway "impeded" results in the buildup of precursor molecules which can then be used in a secondary pathway. This invention is distinct from prior schemes in that the "primary" pathway is being impeded to stimulate a "secondary" pathway, yet the host (which can be a plant or microbe, with *Streptomyces* being a specific example) remains viable and preferably grows normally. With respect to impeding the glycolytic pathway in a host cell, by providing nutrients to the host cell, the impeding pathway results in increases in the production of one or more chemical species in one or more secondary pathways that include D-glyceraldehyde-3-phosphate as a precursor. In one embodiment of the invention, the one or more secondary pathways that include D-glyceraldehyde-3-phosphate as a precursor includes without limitation the clavulanic acid biosynthetic pathway and the non-mevalonate biosynthetic pathway.

By "impeding" it should be understood that the invention contemplates eliminating or disrupting at least one gene coding for at least one enzyme or activity used in a primary pathway, but that the host cell remains viable and preferably functioning (e.g. growing) normally since other genes of the organism (including those in the same pathway coding for the same activity) remain operative. The process results in the accumulation of a precursor that benefits one or more secondary pathways, but does not result in host death (and preferably allows the host cell to function normally) as the host cell maintains genes coding for alternative enzymes or activities which perform the function of the protein coded by the eliminated or disrupted gene.

BRIEF DESCRIPTION OF THE DRAWINGS

FIG. 2: (a) The three conserved motifs of GAPDHs. The accession numbers are as following: *S. coelicolor* (NP_626211.1), *T. tengcongensis* (NP_62335, *T. fusca* (ZP_00059379), *S. aureofacien* (Q59800), *M. tuberculosis* (NP_215952), *B. megaterium* (CAA38376), *M. avium* (P94915), *S. arenae* (P54226), *O. iheyensis* (NP_693359), *S. avermitilis* (NP_827472), *C. tetani* (NP_781078), *B. cereus* (NP_834805). The numbers at two ends indicate the position of amino acids in the proteins, and the numbers between the motifs indicate the separation in amino acid residues. (b) Primers designed for the M1, M2, and M3 motifs according to the CODEHOP program (Rose et al., 1998). N, A/T/G/C; Y, C/T; M, A/C; R, A/G.

FIG. 3A-D. a) Alignment of the deduced S. clavuligerus Gap1 (SEQ ID NO: 43) with homologous GAPDH proteins from other organisms, S. arenae (P54226), S. aureofacien (Q59800), S. coelicolor (NP_626211.1), T. fusca (ZP_00059379), B. halodurans (NP_244427), and C. diphtheriae (NP_939663). Amino acids identical in all aligned proteins are indicated by asterisks (*), and the similar amino acids are indicated by dots (.). The amino acids that have been identified to be important in $NAD^+$-binding and the catalytic mechanism (Skarzynski et al., 1987) are shown in gray and double-underlined; b) nucleic acid sequence encoding Gap1 (SEQ ID NO: 50); c) nucleic acid sequence encoding Gap2 (SEQ ID NO: 53); d) amino acid sequence of Gap2 (SEQ ID NO: 56).

FIG. 5A-C. (a) The organization of gap2 and construction of the gap2 disruption mutant. Restriction maps of the wild-type gap2 gene and its disrupted copy in Gap2-4-14. The solid boxes and arrows represent gap2, the cross-hatched arrows represent the apr cassette. (b) Southern analysis of the gap2:: apr mutant, showing the hybridizing bands to the gap2 probe. (c) Southern analysis of the gap2::apr mutant, showing the hybridizing bands to the apr probe.

FIG. 6. DNA sequence of the PCR product of the gap1::tsr region in gap1 mutant (SEQ ID NO: 54). Sequences of gap1 are in bold and underlined, tsr gene is in capitals, and the sequences from the vector are in lower case.

FIG. 7. DNA sequence of the PCR product of the gap2::apr region in gap2 mutant (SEQ ID NO: 55). Sequences of gap2 are in bold and underlined, and apr gene is in capitals

DETAILED DESCRIPTION OF THE PREFERRED EMBODIMENTS OF THE INVENTION

Figure 1:
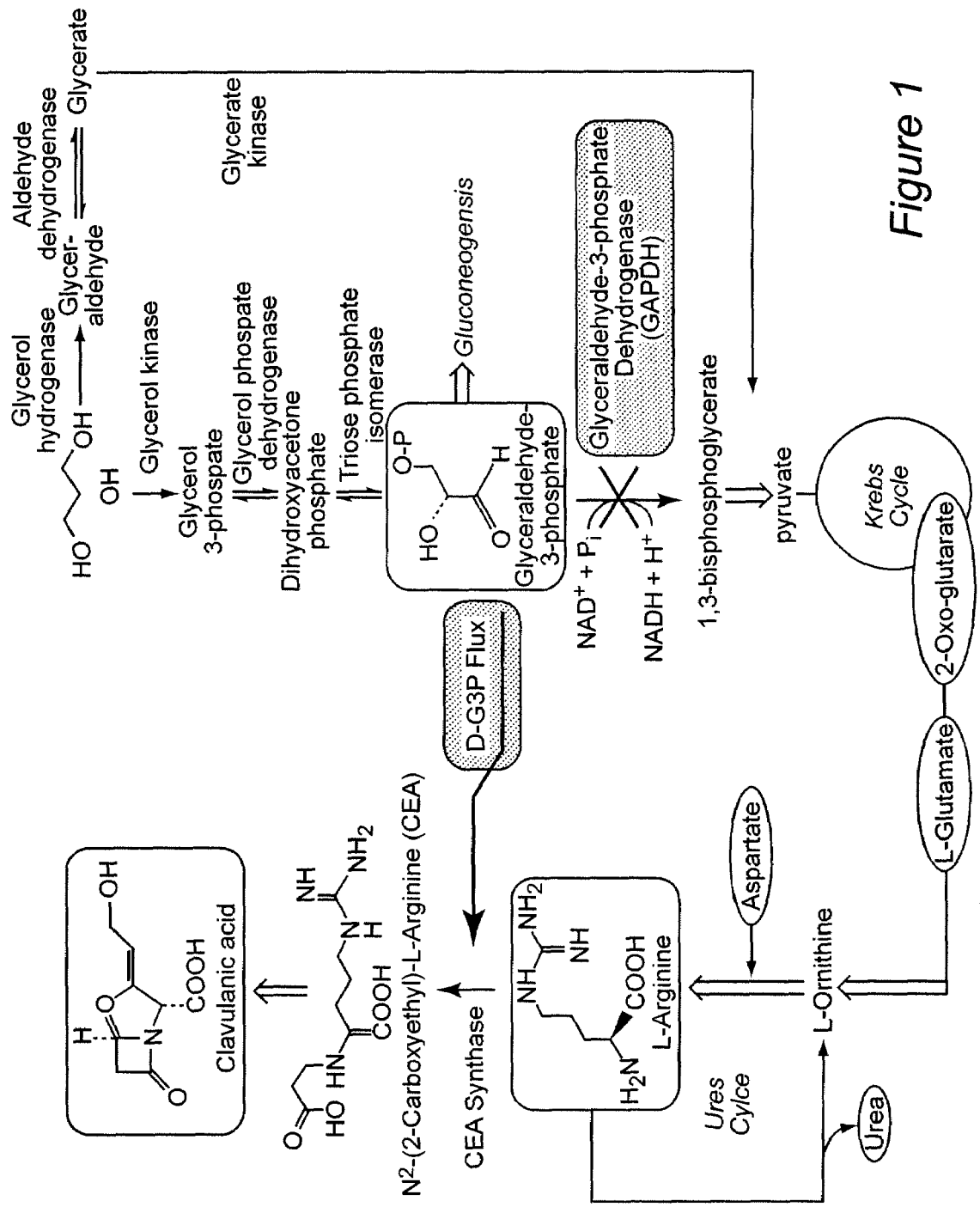
FIG. 1: Clavulanic acid biosynthetic scheme and its precursors showing the carbon flux (some intermediates are omitted). Heavy arrows indicate the $C_3$ precursor flux channeled to the clavulanic acid pathway by targeted gene disruption of gap1.

The present invention provides significant improvements in the production of clavulanic acid by the bacterium S. clavuligerus. To accomplish this, the primary metabolism of S. clavuligerus was manipulated by targeted inactivation of the newly discovered gap1 gene, which encodes glyceraldehyde-3-phosphate dehydrogenase (GAPDH). In the resulting gap1 mutants, clavulanic acid production is dramatically increased in comparison to the non-mutant control. Clavulanic acid production is elevated during the entire fermentation process, and experiments described in the Examples section below demonstrate that this elevation is attributable to the inactivation of gap1. Without being bound by theory, it appears that disruption of gap1 prevents the normal flow of the $C_3$ pool into the glycolytic pathway, resulting in channeling or redirecting of the $C_3$ precursor G3P towards the clavulanic acid pathway instead. Evidence is also provided that, as a result of gap1 inactivation, the $C_3$ pool size in S. clavuligerus is increased to such an extent that L-arginine (not G3P) becomes the rate-limiting precursor for clavulanic acid biosynthesis. This finding led to a further improvement in clavulanic acid production by the intermittent addition of arginine to cultures of S. clavuligerus gap1 mutants. The present invention thus provides a non-standard way of generating higher yields of clavulanic acid, previous methods focusing principally on control mechanisms, e.g. via mutations of regulatory genes.

While the present invention was first demonstrated in S. clavuligerus, those of skill in the art will appreciate that the methodology disclosed herein is applicable to many other organisms. For example, the methodology disclosed herein is readily applicable to other species of bacteria that produce clavulanic acid, for example, Actinomycetes such as various Streptomyces spp., e.g. S. jumonjinensis, S. katsurahamanus, S. lipmanii, etc. (see for example, the review by Jensen and Paradkar, 1999); Pseudomonas spp., etc. Clavulanic acid may be increased in any such species by inactivation of a gene encoding GADPH activity. In addition, the organism that produces clavulanic acid need not be a native or natural producer of this product. Rather, the genes for clavulanic acid synthesis may be inserted into a naive, heterologous host organism (e.g. Escherichia coli, S. coelicolor, S. lividans, S. albus, S. venezuelae, etc.) and the methods of the invention may be carried out in the genetically altered host.

Many varieties of S. clavuligerus have been, are being, or will be developed commercially, especially to increase clavulanic acid production. Typically, these are S. clavuligerus that contain mutations in regulatory genes (e.g. promoter alterations) and that, as a result, have some desired feature such as the ability to synthesize increased amounts of clavulanic acid, increased stability, etc. Such mutant S. clavuligerus strains may also be further genetically engineered by the methodology described herein, to further improve the yield of clavulanic acid from these organisms. Alternatively, S. clavuligerus (and other organisms) that are genetically engineered as described herein to inactivate or attenuate GAPDH may be further engineered in other ways, e.g. by mutations of regulatory genes. All such genetically engineered organisms are intended to be encompassed by the present invention.

Further, inactivation of the gap1 gene in S. clavuligerus to increase clavulanic acid production is illustrative of a broader inventive approach to increasing production of biosynthetic products in living organisms. Accordingly, the present invention provides methodology for increasing production of a biosynthetic product that is produced in an organism by a biosynthetic pathway ("Pathway A"), by inactivating a gene of interest in another pathway ("Pathway B"). The two pathways utilize precursors from a common precursor pool, and compete for precursors from the pool. Inactivation of the gene of interest in Pathway B leads to inhibition of Pathway B, and decreases the channeling of precursors through Pathway B. A buildup of precursors in the pool ensues, making more precursors available for Pathway A. Preferably, Pathway B is non-essential for the organism, or there is a compensatory mechanism in the organism for the activity that is inhibited, so the organism remains viable. For example, another gene that encodes a gene product with the activity may be present and allow Pathway B to function at least partially. Alternatively, another different pathway may be present in the organism (e.g. a "bypass", compensatory, or supplemental pathway) that fulfills the same or a similar function. However, in organisms where Pathway B is essential and there is no compensatory mechanism, the method of the invention can be carried out by partial inhibition of Pathway B. For example, the gene of interest can be genetically modified to be transcribed at a lower level, or so that the transcribed mRNA is translated at a lower level, or so that the gene product is less active. Thus, Pathway B would not be totally eliminated but would utilize less precursor. Excess precursor would then be available for use in Pathway A. Pathway B may, like Pathway A, be a biosynthetic pathway. Alternatively, Pathway B may be a pathway of another type (e.g. catabolic, energy generating, gluconeogenesis, etc.). Further, the methodology need not be confined to a single product produced by a single pathway, and the blocking of a only one gene in only one competing pathway. Rather, according to the methods of the invention, the production of several products (or intermediates) may be increased in one or more pathways, and multiple genes may be inactivated in one or more competing pathways.

Particular examples of other organisms to which the methods disclosed herein apply include but are not limited to *S. coelicolor* and *S. avermitilis*. Whole genome sequences have been published for *S. coelicolor* and *S. avermitilis*, and each of these organisms contains a gap1 and a gap2 gene. The cloning strategy that was used to isolate gap1 and gap2 from *S. clavuligerus* (or other known cloning strategies) could readily be carried out in these organisms, and the methods of the invention could then be applied. Further, as all *Streptomyces*, must have a functioning glycolytic pathway and Krebs cycle to live, it is likely that at least one GADPH-encoding gene is present in other *Streptomyces* (both naive hosts and those producing clavulanic acid) and the principles and methodology taught herein will be widely applicable to such organisms. Further, most if not all microorganisms must have a functioning glycolytic pathway and Krebs cycle to live, and likely possess at least one GADPH-encoding gene that can be inactivated by the methods disclosed herein, in order to augment production of a product or products from competing pathways.

The mevalonate and non-mevalonate biosynthetic pathways are examples of two biosynthetic pathways to which the methods of the present invention can be applied. The mevalonate pathway is responsible for the synthesis of universal terpenoid precursors isopentenyl diphosphate (IPP) and dimethylallyl diphosphate (DMAPP) and is essential in plants, many eubacteria and apicomplexan parasites, but not in archaea and animals. The details of this pathway are well-known. However, another mevalonate-independent pathway for IPP and DMAPP synthesis is also known, although it has been less well characterized (see Eisenreich et al., 2004). The non-mevalonate pathway utilizes glyceraldehyde 3-phosphate (G3P) as a precursor, whereas the mevalonate pathway does not. Thus, inhibiting GADPH activity would lead to a buildup of G3P, which would then be available for use in, e.g., the non-mevalonate pathway.

Those of skill in the art will recognize that ultimately, it is the activity of a gene product of interest (e.g. the gap1 gene product, Gap 1) that is eliminated or attenuated by the methods of the invention. In a preferred embodiment of the invention, this is done by preventing or attenuating expression of the gene that encodes the gene product (e.g. the gap1 gene). As is demonstrated herein, this may be accomplished by disrupting or replacing all or some of the nucleotide sequences of the gene with nucleotide sequences that do not encode a gene product that functions in the pathway, e.g. by targeted gene replacement. In this case, a sufficient portion of the gene sequence must be replaced so that the gene is either not translated at all, or so that the translated gene product is unable to carry out its usual biological function in the pathway that is being blocked.

However, those of skill in the art will recognize that other means are also available to preclude or decrease transcription of a gene. For example, various mutations of the gene sequence, or of sequences necessary for the transcription of the gene sequence, may be carried out, resulting in no or low production of the gene product (e.g. a protein or polypeptide). Examples include but are not limited to point mutations, deletions, additions, replacements, insertions of stop codons, rearrangements, etc. Alternatively, translation of the mRNA encoding the gene product may be prevented or attenuated, e.g. by expressing antisense RNA, or inhibitory or small inhibitory RNA (i.e. RNAi or siRNA), or by inhibiting the translation process in some other manner. In addition, mutations may be introduced into the gene which allow the production of a gene product, but which render the gene product non-functional or of low activity. As a further alternative, the gene product itself may be inhibited from normal functioning, e.g. by exposure to an inhibitor. In all cases, the normal activity of the gene product is prevented or impaired, and the biological pathway in which the gene product normally functions is, as a result, fully or partially inactive. In a preferred embodiment of the invention, the gene of interest is disrupted/inactivated by targeted gene replacement.

By "inactivated" or "attenuated" or "impaired" or "inhibited" or "impeded", we mean that the level or rate of functioning (e.g. transcription and/or translation of the gene of interest, or activity of the gene product) is prevented or altered so that detectable activity of the gene product is decreased by at least about 5%, or about 10%, or about 20%, or about 30%, or about 40%, or preferably by about 50%, more preferably by about 75% to 80%, and most preferably by about 90 or even 95 to 100%, with the caveat that preferably normal growth of the organism is maintained (e.g. growth compared to wild type or a reference strain, or compared to growth of the organism before genetic modification according to the present invention). The decrease in the rate or level of functioning is determined by comparison to the rate or level in, e.g. a wild type or reference strain, or compared to the organism before genetic modification according to the present invention. Those of skill in the art will recognize that the desired level or rate of inactivation may vary from one organism to another, depending on several factors (e.g. whether or not the activity is essential to the organism, whether or not compensatory activities exist, the level of inactivation that is useful to achieve a desired level of production of a biosynthetic product, etc.) Further, this inactivation results in a concomitant inhibition of the pathway in which the gene product normally participates. Therefore, "inactivation" (attenuation, inhibition, impairment, etc.) may be also be used to refer to the pathway that is inhibited. The level of inactivation (disruption, impairment, attenuation, inhibition, etc.) may be detected or measured by any suitable method, e.g. by detecting the gene of interest or mutant forms thereof, by detecting mRNA transcribed from the gene, by detecting an attenuated gene product, by detecting an activity known to be associated with the gene product, by detecting a substance normally produced by the gene product, by detecting the buildup of a substrate or precursor of the gene product, by detecting metabolites or catabolites of the pathway that is inhibited, etc. All such detection or measuring is carried out using suitable controls for comparison, as is well known in the art.

According to the invention, an increase in the production of a biosynthetic product by one biochemical pathway is caused by inhibition of a competing pathway, e.g. by inactivation of a gene of interest in the competing pathway. This results in an "increase" or "elevation" in the amount of the biosynthetic product, by which we mean that at least about 1 to 10%, or about 10 to 25%, or about 25-50%, or even about 50 to 100% more product is produced; or preferably about 100% (i.e. 2-fold) or even more (e.g. 5-10 fold or more) additional product is produced as a result of inhibition of the competing pathway. Those of skill in the art will recognize that such increases may be measured in any of many suitable ways, e.g. by measuring the product itself, by measuring an activity of the product, etc.

Many biosynthetic pathways require one or more precursors (and/or components such as cofactors) in order to carry out the biosynthesis of a single biosynthetic product. For example, the primary metabolic precursors of clavulanic acid are G3P and L-arginine. Thus, when the available pool of one precursor for a biosynthetic reaction is increased by the methods of the invention, it may also be beneficial to supply other precursors at an increased concentration. This may be accomplished by any available means (e.g. by genetic engineering of the host organism to increase production of the other precursors; by addition of the precursor to the media in which the host organism is grown; by increasing the concentration of a substance that, in turn, increases precursor production, etc.). In one embodiment of the invention, the level of G3P available to the clavulanic acid biosynthetic pathway is increased by the methods of the invention, and the concentration of L-arginine is increased by supplementing the media in which the host organism (e.g. *S. clavuligerus*) is grown. Those of skill in the art will recognize that the level and frequency of supplementation will vary depending on the biosynthetic pathway and the precursor that is being supplemented. For supplementing *S. clavuligerus* mutants as described herein with L-arginine, in one embodiment, the media in which the *S. clavuligerus* is grown is supplemented with L-arginine at a concentration of from about 0.1 to about 100 mM, and preferably from about 0.1 to about 50 mM, and most preferably from about 1 to about 20 mM. In one embodiment, 13.5 mM of L-arginine is used. In addition, the frequency of supplementation may vary, but for bacteria, will generally be carried out in the range of from about every 1 to 24 hours or longer. In addition, supplementation may be continuous, or the additional supplement may be included in the original media, i.e. all at once at the beginning of culture. In one embodiment, supplementation is once every 24 hours.

In some embodiments of the invention, the production of one biosynthetic product is increased by the methods of the invention. However, this need not be the case. Manipulation of a biochemical pathway may result in increased production of more than one biosynthetic product, from one or more different biosynthetic pathways. In addition, the invention is not limited to inhibiting one pathway in an organism. Rather, several biochemical pathways in an organism may be inhibited in order to increase production of a product or products, so long as the organism remains viable.

In one embodiment of the invention, the gap1 gene disclosed herein can also be used as a diagnostic tool to identify related genes in other organisms. Those of skill in the art are acquainted with techniques for doing so, e.g. by designing primers based on the gap1 sequence, for example, primers that are unique to gap1, and using the primers to amplify DNA from other organisms suspected of containing a related GAPDH gene by polymerase chain reaction (PCR), e.g. via the CODEHOP technology. The invention thus also provides the sequence of gap1 (SEQ ID NO: 50) and encompasses nucleic acid sequences that are at least about 50, 60, 70, 80, 90 or even 95% homologous to gap1. Complementary DNA sequences are also contemplated, as are RNA sequences that can be transcribed from the gap1 gene, and primer sequences that can be used to specifically amplify gap1 by PCR, or to otherwise detect gap1. In a preferred embodiment, the invention also provides DNA and/or RNA sequences that encode the Gap1 protein (SEQ ID NO: 43), or protein sequences that display at least about 30, 40, 50, 60, 70, 75, 80, 85, 90, or even 95% or more identity with SEQ ID NO: 43. Those of skill in the art are familiar with techniques for establishing levels of identity when comparing protein/polypeptide sequences, and would be able to readily ascertain whether or not a protein meets this criteria.

The gap1 gene or portions thereof may be used to identify homologous genes in other organisms, or for comparisons to other gene sequences, for example, to identify whether or not a functional gap1 (or homologous) gene is present in an organism. The Gap 1 protein may also be useful for similar purposes.

EXAMPLES

Clavulanic acid is a potent β-lactamase inhibitor used to combat resistance to penicillin and cephalosporin antibiotics. There is a demand for high-yielding fermentation strains for industrial production of this valuable product. Clavulanic acid biosynthesis is initiated by the condensation of L-arginine and D-glyceraldehyde-3-phosphate (G3P). To overcome the limited G3P pool and improve clavulanic acid production, the glycolytic pathway in *Streptomyces clavuligerus* was genetically engineered. Two genes (gap1 and gap2) whose protein products are distinct glyceraldehyde-3-phosphate dehydrogenases (GAPDHs) were inactivated in *S. clavuligerus* by targeted gene disruption. A doubled production of clavulanic acid was consistently obtained when gap1 was disrupted, and reversed by complementation. Addition of arginine to the cultured mutant further improved clavulanic acid production giving a greater than 2-fold increase over wild-type, suggesting that arginine became limiting for biosynthesis.

2. Materials and Methods 2.1. Bacterial Strains, Plasmids, Media, and Bacteriological Techniques.

The bacterial strains and plasmids used in this study are listed in Table 1. *Escherichia coli* and *Streptomyces* strains were grown as described by Sambrook, Kieser, and Li (Kieser et al., 2000; Li et al., 2000; Sambrook et al., 1989). For clavulanic acid production in batch cultures, mycelia from the seed cultures were transferred into either starch-aspargine (SA) (Paradkar and Jensen, 1995), PES medium (per liter: glycerol 20 g; protein extract from soybean 5.5 g; K2HPO4 0.8 g; MOPS 21 g; pH 7.0) or PES2 medium (per liter: soluble starch 20 g; asparagine 2 g; protein extract from soybean 5.5 g; K2HPO4 0.8 g; MOPS 21 g; pH 7.0) at the ratio of 1:20. The fermentation cultures were grown under the same conditions as the seed culture (Li et al., 2000).

TABLE 1

Bacterial strains and plasmids

| Strain or plasmid | Relevant characteristics | Reference or source |
|---|---|---|
| Strains | | |
| *E. coli* | | |
| DH5α | F- recA1 gyrA96 thi-1 hsdR17 supE44 relA1 deoR (lacZYA- argF)U196 φdlacZΔM15 | Invitrogen |
| JM110 | dam dcm supE44 thi leu rpsL lacY galK galT ara tonA thr Tsx Δ(lac-proAB) F'[traD36 proAB+lacZΔM15 | Stratagene |
| Gap-195 | DH5α transformant containing 3.5 kb gap1 cluster | This study |
| ESS | β-lactam-supersensitive indicator strain | (Aoki et al., 1976) |
| *K. pneumoniae* Subsp. *pneumoniae* ATCC 29665 | Indicator strain for clavulanic acid bioassay | (Romero et al., 1984) |
| *S. clavuligerus* | | |
| ATCC 27064 | clavulanic acid producer, wild-type strain | ATCC[a] |
| Gap15-7-30 | gap insertional disruption mutant (gap::tsr) | This study |
| Gap15-7-30 (pSET152) | Gap15-7-30 with plasmid pSET152 | This study |
| Gap15-7-30 (1-95) | Gap15-7-30 with plasmid pSET152/1-95 | This study |
| *S. coelicolor* CH999 | Strain used as control for PCR cloning of gap | ATCC |
| *Bacillus* sp. ATCC 27860 | Indicator strain used for clavam bioassay | (Pruess and Kellett, 1983) |
| Plasmids | | |
| pBluescript II SK (−) | Phagemid; Amp[R] | Stratagene |
| pKC1139 | *Streptomyces-E. coli* bifunctional vector, Am[R] | (Bierman et al., 1992) |
| pIJ680 | High-copy-number *Streptomyces* cloning vector, Thio[R], Neo[R] | (Kieser et al., 2000) |
| pWHM3 | High-copy-number *Streptomyces - E. coli* bifunctional Vector derived from pIJ486, Thio[R] | (Vara et al., 1989) |
| pWHM3Am | High-copy-number *Streptomyces-E. coli* bifunctional vector, Apr[R] | This study |
| pSET152 | *Streptomyces-E. coli* bifunctional integrative vector, Am[R] | (Bierman et al., 1992) |
| pBSGAP | pBluescript II SK (−) containing the 510 bp gap PCR product | This study |
| pBSGAPT | pBSGAP containing tsr-disrupted gap PCR product | This study |
| pGAPT | pWHM3Am containing the tsr-disrupted gap PCR product | This study |
| pBS/1-95 | pBluescript II SK (−) containing the 3.5 kb fragment hybridizing to 510-bp gap probe | This study |
| pSET152/1-95 | pSET152 containing the 3.5-kb gap fragment | This study |
| pBSGAP2 | pBluescript II SK (−) containing the 510 bp gap2 PCR product | This study |
| pBAGAP2Am | pBSGAP2 containing apr-disrupted gap2 PCR product | This study |
| pGAP2Am | pWHM3 containing the apr-disrupted gap2 PCR product | This study |

[a]ATCC, American Type Culture Collection 2.2. Cloning the Gap Genes

PCR primers were designed by the CODEHOP strategy (Rose et al., 1998) according to the highly conserved motifs found in putative GAPDH proteins that showed highest homology to *S. coelicolor* GAPDH (website located at www.sanger.ac.uk/Projects/S_coelicolor/) in a BLASTP analysis (FIG. 2). The components of reaction mixture were as described by Stratagene. The PCR reaction was performed using a "touchdown" program which consisted of (1) denaturation at 98° C. for 2 min, (2) 7 cycles of 40 sec at 98° C., 1 min at 63-57° C. (decreasing 1° C. every cycle) and 40 sec at 72° C., (3) 30 cycles of 40 sec at 98° C., 1 min at 56° C. and 40 sec at 72° C., and (4) 10 min at 72° C. The 510-bp products, amplified with the Gap-Deg-5/Gap-Deg-3 primers, were cloned into pBluescript II SK(−) (pBSG510). To clone the whole gap1 gene, the genomic DNA of *S. clavuligerus* was digested with BamHI, BglII, EcoRI, PstI, XbaI-HindIII, or XbaI-XhoI, and probed with the 510-bp partial gap1 (May, 1998; Sambrook et al., 1989). A sub-genomic library was constructed by ligating the 3-5 kb BglII genomic DNA fragments of *S. clavuligerus* with pBluescript II SK(−). The positive clones were identified by colony hybridization (Sambrook et al., 1989). To clone the whole gap2 gene, genomic DNA of *S. clavuligerus* was digested with BglII, ClaI, EcoRI-HindIII, KpnI, NcoI, NotI, PstI, SacI, ScaI, or XbaI-XhoI, and probed with the 510-bp gap2 PCR. A sub-library was constructed by ligating the 3-5 kb fragments of NcoI digested genomic DNA with pGEM®-5Zf(+). Positive clones were selected by colony hybridization using the 510-bp gap2 probe.

2.3. Recombinant DNA Procedures

All plasmids and genomic DNAs were isolated and purified using standard methods (Kieser et al., 2000; Sambrook et al., 1989) or as described by the manufacturer.

To construct pWHM3 Am, a replicationally unstable bifunctional vector in *Streptomyces*, the apramycin resistance gene was recovered as a 1.5-kb EcoRI-PstI fragment from pKC1139. A 1.1-kb fragment containing about 600-bp corresponding to the thiostrepton resistance gene (tsr) was deleted from pWHM3 (Vara et al., 1989), and the remaining part of the plasmid was blunt-ended with Klenow DNA polymerase and ligated into the apr cassette.

pGAPT was constructed as follows. The 1.1-kb tsr fragment was excised by digestion of pIJ680 with BclI. The blunt-ended tsr fragment was ligated into the unique BlpI internal site of the 510-bp gap PCR product in pBSGAP to give the pBSGAPT. The 1.6-kb tsr-disrupted gap fragment was excised and inserted into the unique ClaI site of pWHM3Am by blunt ligation to generate the disruption vector pGAPT. pGAPT was transformed into the methylation-deficit strain of *E. coli* JM110 before transforming into *S. clavuligerus*.

To complement the gap1::tsr mutant, pSET152/1-95 was constructed as follows. The 3.5-kb fragment containing the whole gap gene and the upstream regulatory elements was excised from a positive hybridizing clone of the sub-library pBS/1-95 by XbaI-EcoRV and ligated into the site-specific integrative vector pSET 152. The resulting vector, pSET152/1-95 was transformed into *E. coli* JM110, from whence the plasmid DNA was prepared and used for the transformation of the gap1 disruption mutant.

To construct pGAP2 Am, the 1.5-kb blunt-ended apramycin resistance cassette (apr) was inserted into the unique NruI site in the 510-bp gap2 fragment in pBSGAP2 to give pBSGAP2 Am. The 2.1-kb apr disrupted gap2 fragment was excised and ligated into the blunt-ended XbaI site of pWHM3 to generate pGAP2 Am. To overcome the restriction barrier, pGAP2 Am re-isolated from *E. coli* JM110 was used to transform *S. clavuligerus*.

2.4. Transformation of *S. clavuligerus* and Gene Disruption

Protoplast formation, DNA transformation, and selection and confirmation of double-crossover mutants of *S. clavuligerus* were carried out as described previously (Li et al., 2000). Two primers were designed according to the 510-bp gap sequence to confirm the double crossover event in gap1 disruption mutants by PCR. CLAGAP5, CACGCCTCCTG-TACCACCAACTGTG (SEQ ID NO: 51), and CLAGAP3, TGGAGTAGCCCCACTCGTTTCATACC (SEQ ID NO: 52). The PCR reaction was carried out using the standard protocol (Sambrook et al., 1989).

2.5. DNA and Protein Analyses

All DNA sequencing was carried out in the Peptide/Protein Facility, The Johns Hopkins University School of Medicine (Baltimore, Md.). PSIPRED Protein Structure Prediction Server (website located at bioinf.cs.ucl.ac.uk/psipred/) was used for secondary structure prediction, and the Swiss-Model server (website located at swissmodel.expasy.org/SWISS-MODEL.html) was used for homology modeling.

2.6. Fed-batch Culture

Chemical feeding experiments were preformed as described by Chen et al. (Chen et al., 2003). Starting after 60 h of batch culture, arginine or glycerol was fed every 24 h to a final concentration of 13.5 mmol and 0.5 mmol, respectively. Samples were withdrawn and analyzed for clavulanic acid titer at intervals of 24 h to 192 h of fermentation.

2.7. Analysis of β-lactam Antibiotics

A 2-ml sample was taken every 24 h from each culture during the fermentation process. The cell pellet was used to determine the wet weight as the biomass, and the supernatant was used for assays of clavulanic acid, cephamycin C or antipodal clavams (Aoki et al., 1976; Pruess and Kellett, 1983; Romero et al., 1984). Clavulanic acid and its bicyclic β-lactam-containing co-metabolites were also analyzed by reaction with imidazole (Bird et al., 1982). Filtered fermentation supernatant (90 μl) was reacted with 30 μl of 3 M imidazole solution (pH 6.8) at 37° C. for 40 min. The imidazole derivative was diluted 15-fold with ddH$_2$O and its absorbance was measured at 312 nm. Clavulanic acid yields in *S. clavuligerus* strains were determined by comparison to a calibration curve generated from a pure standard of clavulanic acid. Clavulanic acid was also analyzed by high-pressure liquid chromatography (HPLC) using a Hewlett-Packard Series 1050 HPLC system. A 50-111 imidazole derivative was analyzed on a Phenomenex Prodigy ODS(3) column (250 mm×4.6 mm) (Torrance, Calif.) at 312 nm. The mobile phase consisted of 0.1 M KH$_2$PO$_4$ (pH 3.3 adjusted with H$_3$PO$_4$) and 6% CH$_3$OH (flow rate 1 ml/min).

2.8. Nucleotide Sequence Accession Numbers

The GenBank accession number for gap1 is DQ178995, gap2 is DQ178997, and pgk is DQ178996. The amino acid sequence of Gap1 protein (SEQ ID NO: 43) is shown in FIG. 3A, and the nucleic acid sequence of gap1 (SEQ ID NO: 50) is shown in FIG. 3B.

3. Results 3.1. Cloning of the Gap Genes from *S. clavuligerus*

The GAPDHs involved in glycolysis in prokaryotic organisms belong to the phosphorylating GAPDH family (Mateos and Serrano, 1992), whose primary amino acid sequences show considerable homology (Mateos and Serrano, 1992). BLASTP analysis revealed a group of GAPDHs from different organisms having high homology, including proteins from four *Streptomyces* strains. The similarities among these organisms were reduced to three short motifs: (H/Q)(H/T/N)(V/I)S NASCTTN (motif M1, SEQ ID NO: 57), (S/K/R)D(L/Y/P)RRARAAA (motif M2, SEQ ID NO: 58), and WYDNE(S/W/T) G(Y/F)S(H/A/H/T) (motif M3, SEQ ID NO: 59) (FIG. 2*a*). Using the recently developed CODEHOP program (Rose et al., 1998), we designed two forward primers for the M1 and M2 motifs and one reverse primer for the M3 motif (FIG. 2*b*). A distinct band with the expected size of 510 bp was obtained from both *S. clavuligerus* and *S. coelicolor* chromosomal DNA with Gap-Deg-5/Gap-Deg-3 primers, while no PCR product was detected when Gap-Deg-5-2/Gap-Deg-3 primers were used, presumably due to the high Tm value of the Gap-Deg-5-2 primer. The 510-bp product was cloned and nine randomly selected clones were sequenced.

DNA sequence analysis revealed that two PCR products were indeed present in the 510-bp PCR band. BLASTX analysis of the first PCR product, which was obtained from seven clones, showed that the amino acid sequence from one translated frame had high homology to the M1 and M2 motifs conserved in GAPDHs. A positive band of approximately 3.5 kb was identified in a Southern hybridization from BglII digested chromosomal DNA by using the 510-bp PCR product as probe. A sub-genomic library generated from the 3-5 kb BglII gDNA fragments was screened by colony hybridization. Of 320 colonies screened, 4 positive clones were identified. Restriction mapping revealed a 4.0-kb insert in these clones. One of them, clone Gap-195, was sequenced on both strands.

FramePlot (Ishikawa and K. Hotta, 1999) analysis of the DNA sequence of clone1-95 revealed one incomplete and two complete open reading frames (ORF). The first ORF, gap1, encodes a 355-amino acid protein with a predicted molecular weight (MW) of 36 009 Da and the isoelectric point (pI) of 4.83. A BLASTP search showed that Gap1 has significantly high similarity (94 to 57% identity and 97 to 72% similarity) to GAPDHs from a number of microorganisms. The greatest similarities are to the putative GAPDHs from *S. avermitilis* MA-4680 (92% identity and 97% similarity) and *S. coelicolor* A3(2) (94% and 96%, respectively). Gap 1 possesses all three conserved motifs and almost all the amino acid residues thought to be required for NAD+–binding (Gly11, Arg12, Asp35, Phe101, and Ala122) and catalysis (Cys153 and His180) (FIG. 3*a*) (Skarzynski et al., 1987). Homology modeling demonstrated a significantly high structural similarity between Gap1 and other GAPDHs (not shown). These comparative analyses strongly suggested that gap1 encodes GAPDH in *S. clavuligerus*.

Downstream of gap1 lies the second ORF encoding a protein of 403 amino acids with the calculated MW of 41 923 Da and pI of 4.89. A BLASTP search showed that the deduced amino acid sequence of the encoded protein is highly homologous to 3-phosphoglycerate kinases (Pgk) from several *Streptomyces* strains and many other organisms. The greatest similarity was found to the Pgk from *S. coelicolor* A3(2) (85% identity and 92% similarity). Multiple sequence alignment and secondary structure prediction between *S. clavuligerus* Pgk and homologous proteins revealed a high degree of conservation in 14 β-sheets and adjacent peptide segments that are involved in the formation of inner loops in the substrate-binding cleft present in all Pgk proteins (Hong et al., 2000).

A second PCR product was present in two of the nine clones sequenced. Southern hybridization of genomic DNA digested with restriction enzymes revealed that the gene was located in a 4~5-kb NcoI gDNA region. 900 clones in a sub-library constructed and screened by colony hybridization, and two positive clones were identified. FramePlot analysis showed one complete ORF (gap2) was present in the sequenced region. The encoded protein is composed of 481 amino acids with a predicted molecular weight (MW) of 52 354 Da and pI of 6.43. The deduced Gap2 protein contains the conserved M1 and M3 motifs and shows significant similarity to a group of putative glyceraldehyde-3-phosphate dehydrogenases, including Gap2 in *S. coelicolor* (89% identity and 95% similarity), and GapX in *S. roseofulvus* (86% identity and 92% similarity). The residues from 135 to 300 show similarity to NAD+binding domains that usually encompasses amino acids 1-150 in GAPDHs. Residues 300-460 show similarity to C-terminal catalytic sites in GAPDHs (Skarzynski et al., 1987). Interestingly, the overall homology between Gap1 and Gap2 is significantly low (25% identity and 37% similarity) except within the conserved motifs.

3.2. Disruption of Gap1 and Gap2 in *S. clavuligerus*

To investigate whether gap1 and gap2 are essential for *S. clavuligerus* survival and if an increased intracellular pool of G3P can increase precursor flux to clavulanic acid, two mutants were generated by targeted gene replacement. The 510-bp gap1 PCR product was disrupted in vitro by insertion of the thiostrepton resistance cassette (tsr); the disrupted gene was then inserted into pWHM3AM, and the resulting vector, pGAPT, was introduced into *S. clavuligerus*. The primary transformants were subjected to two rounds of sporulation and the progeny were screened for the AmS/ThioR phenotype expected for a double-crossover event between the disrupted gene and its chromosomal counterpart. Five hundred colonies were screened and two showed the AmS/ThioR phenotype. One of them, Gap15-7-30, was used for further investigation.

*S. clavuligerus* protoplasts were transformed with the recombinant plasmid pGAP2Am, which confers thiostrepton resistance and also carries the 510-bp gap2 disrupted by an apramycin resistance gene. Because the transformants showed poor sporulation on the tested media, they were subjected to protoplast formation and regeneration to allow homologous recombination and vector elimination. Progeny screened for the loss of thiostrepton resistance yielded strains with the ThioS/AmR phenotype. 350 clones were screened for double crossover in this case and three ThioS/AmR strains were obtained. One of them, Gap2-4-14 was used for the subsequent studies.

Figure 4A:
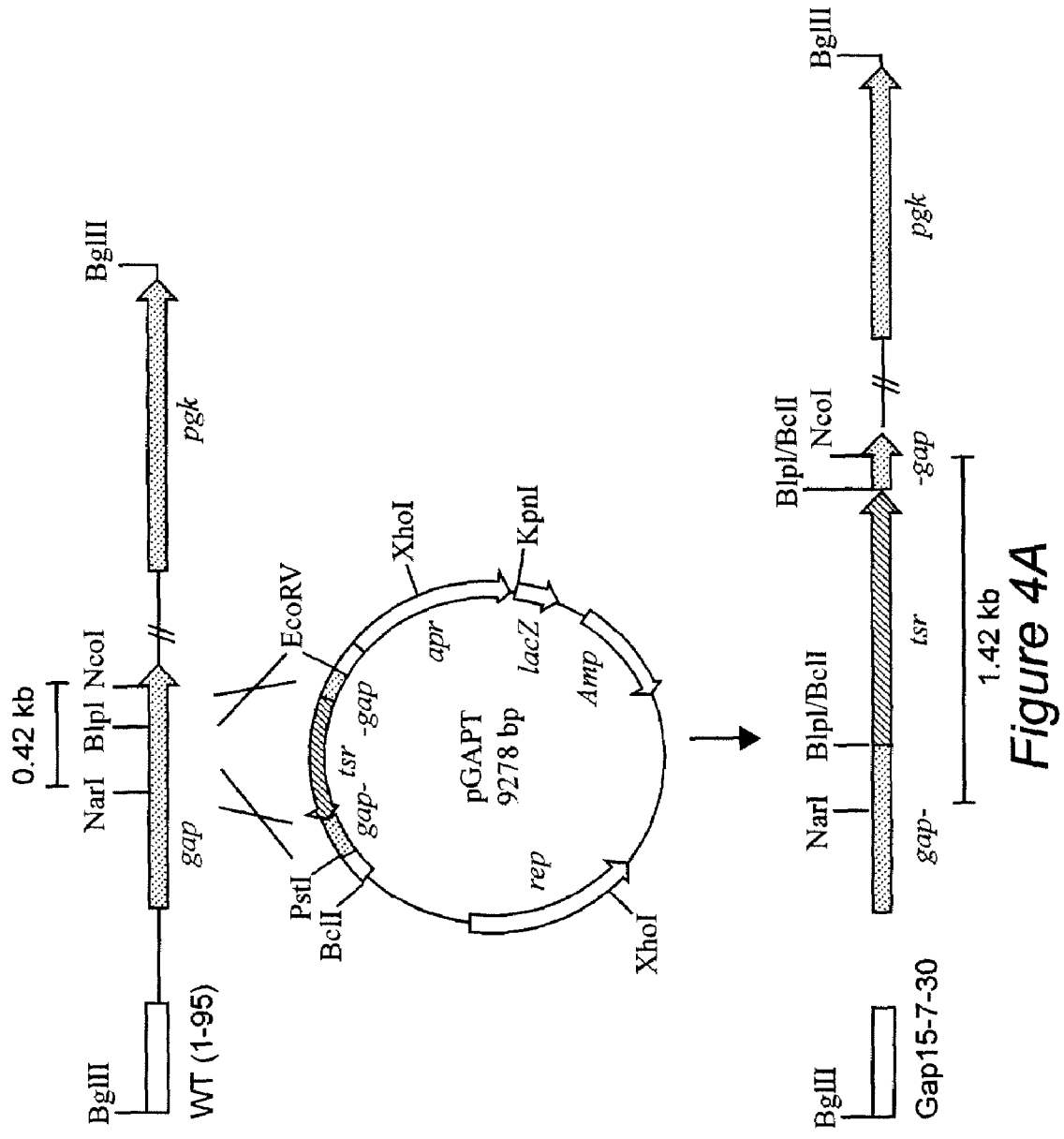
FIG. 4A-C. (a) The organization of gap1 and pgk in clone 1-95 and construction of the gap1 disruption mutant. The restriction maps of the wild-type gap1 gene and its disrupted copy in the mutant are shown, and the expected band sizes in the Southern hybridization. The solid boxes and arrows represent gap1, the cross-hatched arrows represent tsr cassette, and the dark grey arrows represent the pgk gene. (b) Southern analysis of gap1::tsr mutant, showing the hybridizing bands to the gap probe. (c) Southern analysis of gap 1::tsr mutant, showing the hybridizing bands to the tsr probe.
Figures 4B, 4C:
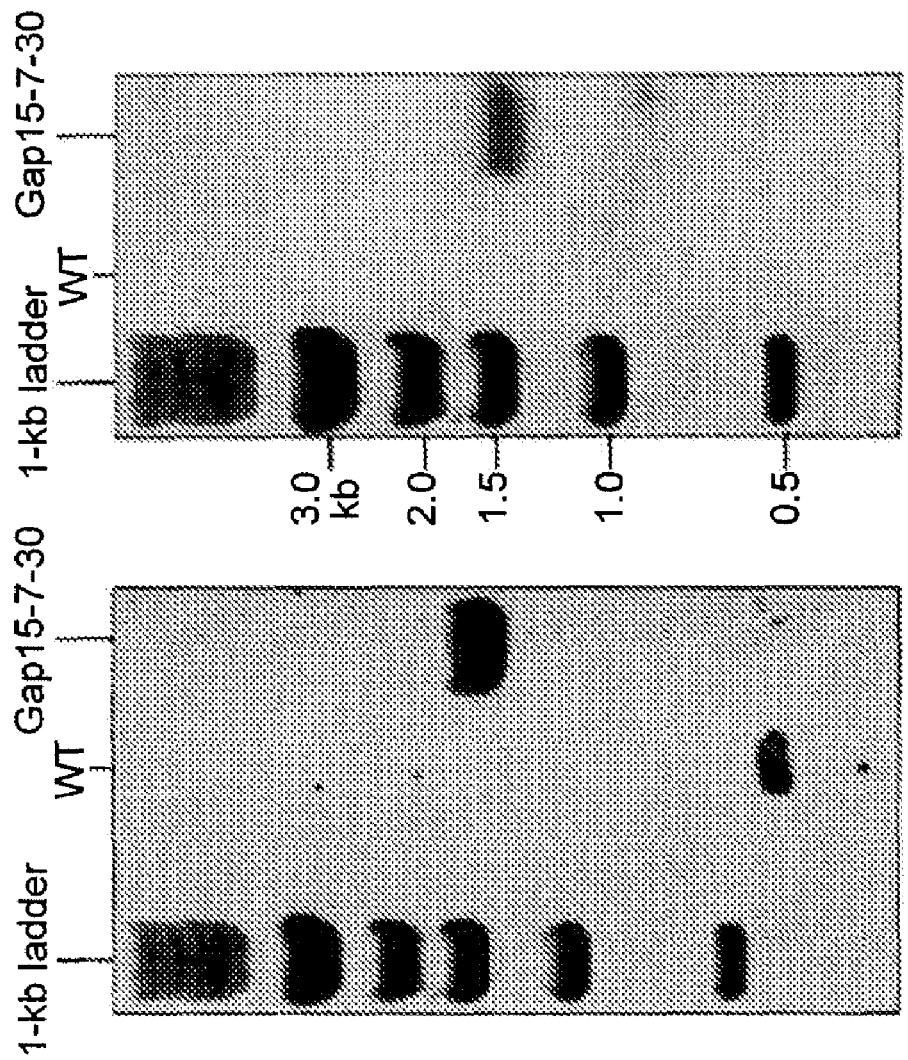
Figure 5A:
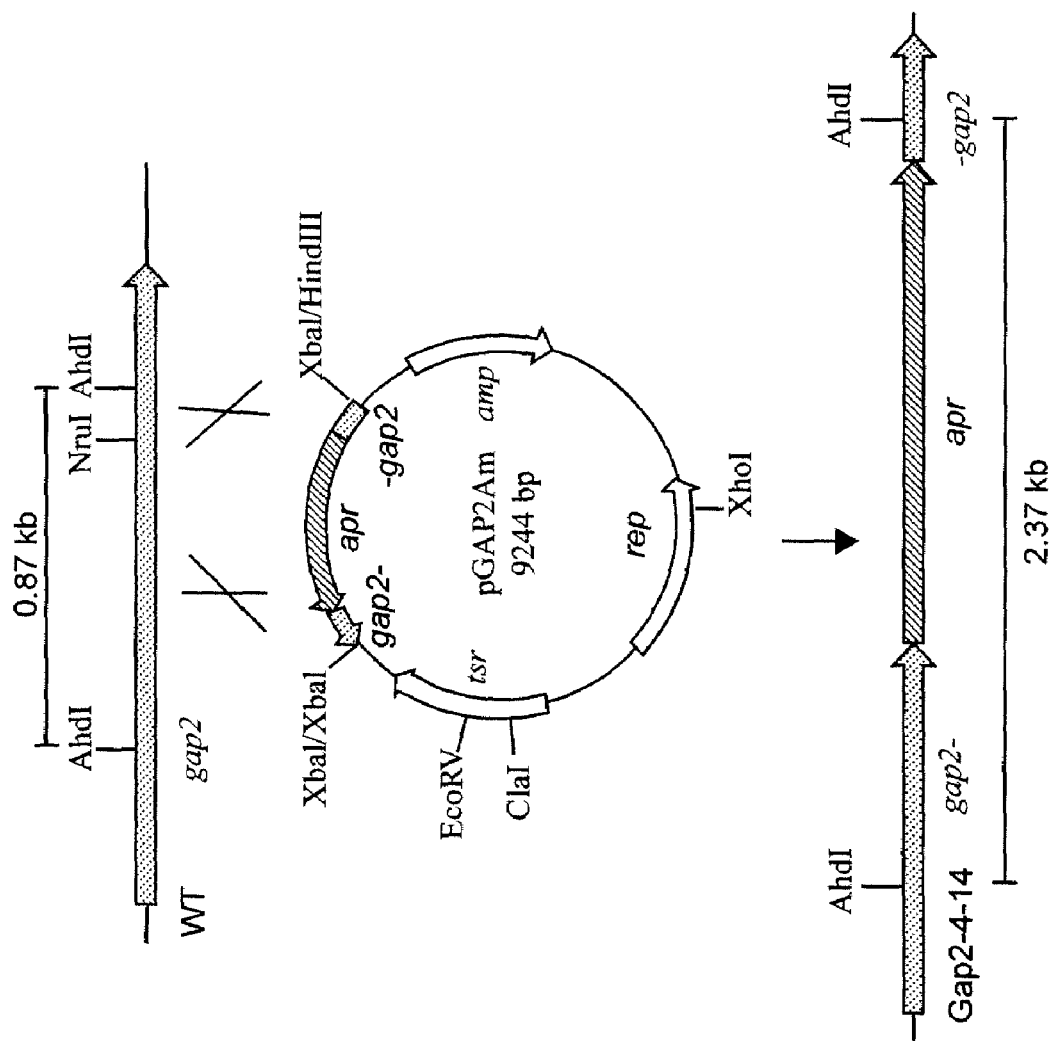

The replacement of wild-type gap1 and gap2 in Gap15-7-30 and Gap2-4-14 and subsequent plasmid elimination were confirmed by both PCR amplification and sequencing of the disrupted region, and analysis by Southern hybridization. A specific 1.5-kb PCR product was obtained from Gap15-7-30 genomic DNA, corresponding to the sum of the gap1 fragment and the tsr cassette, whereas under the same conditions the wild-type genomic DNA gave a 0.5-kb PCR product. DNA sequencing confirmed that the PCR product contained the gap1 fragment disrupted by the tsr cassette at a BlpI site (data not shown). Chromosomal DNA isolated from the wild type and Gap15-7-30 were separately digested with NarI-NcoI and hybridized to gap1-specific and tsr-specific probes. As expected, the gap1 probe gave a 0.4-kb hybridization band in the wild-type genome, and this band was replaced by a 1.4-kb band in the Gap15-7-30 genomic hybridization. Gap15-7-30 gave exactly the same hybridization pattern to the tsr probe as the gap1 probe, but no hybridization band was seen from the wild-type genomic DNA (FIG. 4). Thus, the wild-type gap1 had been replaced by the tsr-disrupted copy in Gap15-7-30 in a double-crossover event. To confirm the double-crossover event in Gap2-4-14, genomic DNA isolated from wild-type and Gap2-4-14 were digested with AhdI and hybridized with gap2-specific and apr-specific probes. Gap2-4-14 consistently gave a 2.4-kb positive band to both gap2 and apr probes, corresponding to the predicted size of gap2::apr, whereas the wild-type gave a 0.9-kb hybridization band to gap2 probe, and no hybridization occurred to apr probe. These results demonstrated that the wild-type gap2 has been replaced by an apr-disrupted copy in Gap2-4-14 (FIG. 5).

3.3. Analysis of the Gap15-7-30 and Gap2-4-14 Mutants

The Gap 15-7-30 and Gap2-4-14 mutants were then characterized to determine the effect of the mutations on clavulanic acid production. The mutants were cultivated on PES, PES2 and SA media as batch cultures, and samples were withdrawn every 24 h during incubation to assess secondary metabolite yields by bioassay, imidazole derivatization, and HPLC analysis. The fermentation was repeated four times, and the performance of the Gap 15-7-30 culture was observed to be highly reproducible. All mutant cultures were compared to similarly grown wild-type *S. clavuligerus* control cultures. Cell density was measured as wet weight. As shown in FIG. 6*a*, the biomass of Gap 15-7-30, Gap2-4-14 and the wild-type strain were quite similar in all media tested. Microscopic observation of mycelia of both wild-type and two mutants did not show any distinct morphological differences, indicating that inactivation of gap1 and gap2 had no detectable effects on the morphology of *S. clavuligerus*.

Figure 8A:
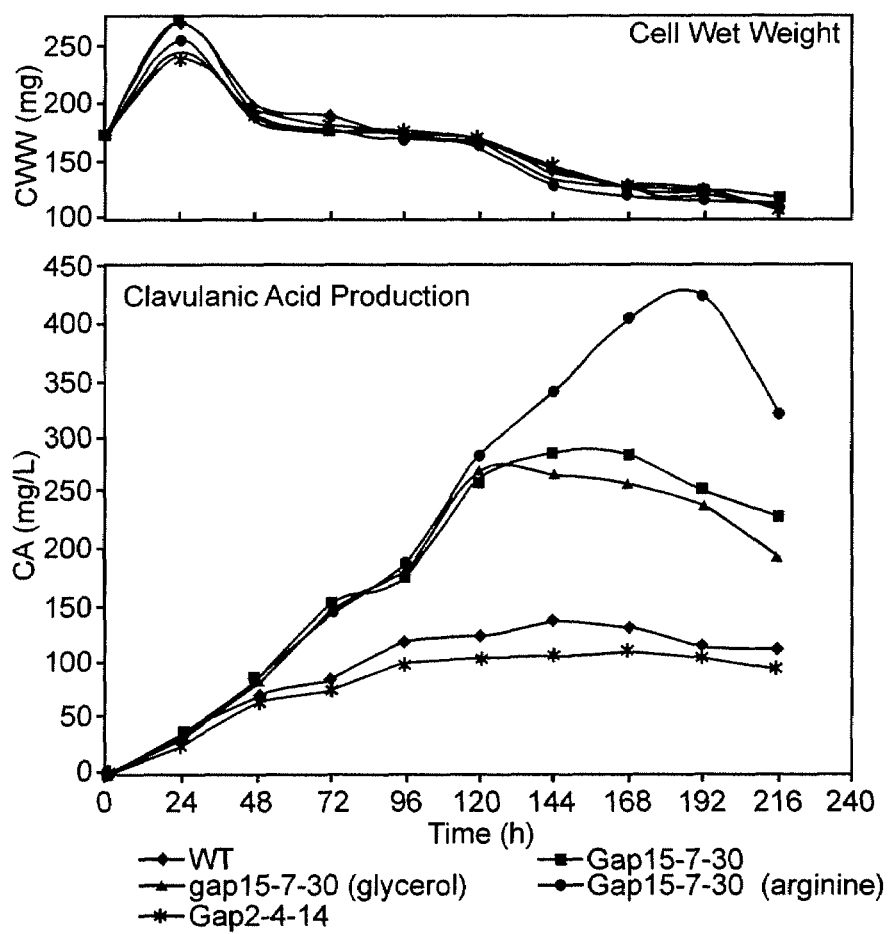
FIG. 8: (a) Time course of clavulanic acid production and biomass in batch cultures of PES medium. (b) HPLC analysis of clavulanic acid production (as its imidazole derivative, tR=5.4 min.) in wild-type, Gap15-7-30, and Gap15-7-30 (1-95).
Figure 8B:
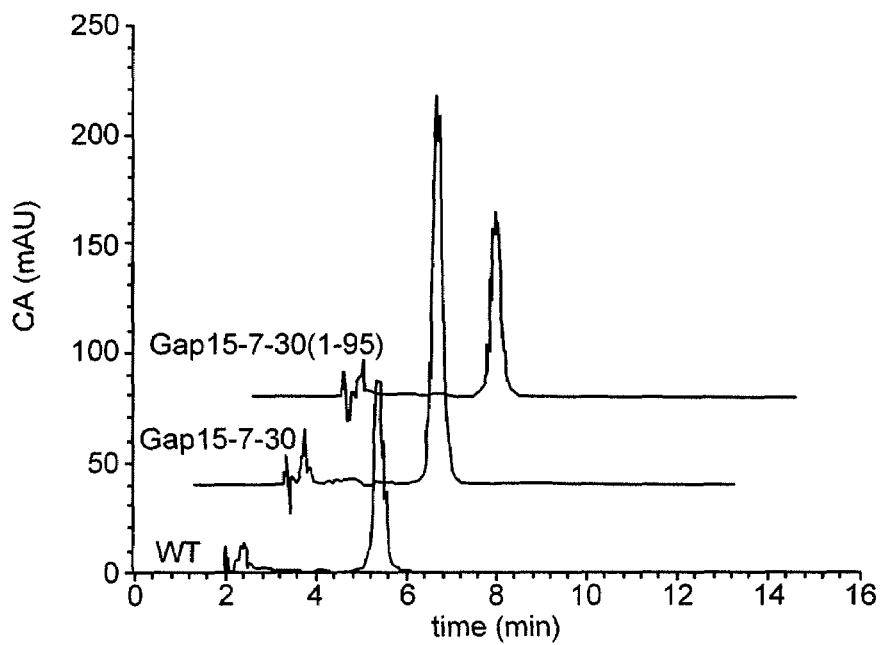

Bioassay with the β-lactam supersensitive *E. coli* ESS showed that wild-type and both mutants produced similar levels of cephamycin, indicating the disruption of gap1 and gap2 had no effect on cephamycin biosynthesis (data not shown). The time course of clavulanic acid production in PES batch cultures in shake-flasks was measured by both imidazole derivatization followed by UV and HPLC chromatographic analyses. In PES medium the wild-type and two mutants produced similar levels of clavulanic acid in the first 48 h of fermentation. Over several fermentations, the maximal production of clavulanic acid in wild-type *S. clavuligerus* was between 120 and 135 mg/L. The production in Gap15-7-30 started increasing from 48 h and reached a maximum at a range of 260 to 282 mg/L, a 110% increase over the wild-type strain. The higher production was maintained between 80% and 110% over the wild-type strain until the end of the fermentation (216 h) (FIG. 8a). Enhanced clavulanic acid production in Gap15-7-30 has been consistently obtained from repeated fermentations under identical conditions. Bioassay on *K. pneumoniae* plates showed an increased inhibition zone from the Gap 15-7-30 supernatant, consistent with the increased production of clavulanic acid. When culture supernatants were reacted with imidazole, HPLC analysis revealed that the peak corresponding to the chromophoric derivative of clavulanic acid (tR 5.4 min) was increased in Gap 15-7-30, quantifying the elevated production (FIG. 8b). The increased clavulanic acid production was also observed in PES2 and SA media. In contrast to the PES medium, growth in PES2 medium showed no onset of production occurring in the late exponential phase of growth. In contrast clavulanic acid was produced throughout the growth phase, but only about 20% more was obtained over the wild-type in PES2 medium at its peak (data not shown). In SA medium, the maximal clavulanic acid production in Gap15-7-30 was also only about 20% greater than the wild-type (data not shown).

We tested the stability of the gap1::tsr mutant by passing Gap 15-7-30 through five generations without selective antibiotic pressure. The progeny still showed the same level of thiostrepton resistance and enhanced production of clavulanic acid in PES medium. Thus, the double-crossover in Gap15-7-30 is genetically stable (data not shown).

The effect of inactivation of gap2 on clavulanic acid productivity was similarly investigated in both PES, and PES2 media. The mutant produced similar amounts of cephamycin and clavams as the wild-type strain as indicated by bioassays on *E. coli* ESS and *Bacillus* sp. 27860 plates (data not shown). In PES medium, a consistent 20-30% decreased clavulanic acid production in Gap2-4-14 was observed after 72 h of fermentation (FIG. 8a), whereas in PES2 medium the disruptant produced a similar level clavulanic acid as the wild-type strain (data not shown).

3.4. Complementation of the Gap15-7-30 Disruption Mutant

We assumed that increased clavulanic acid production was due to the build up of G3P in the gap1 disruption mutant. To confirm this, an in trans complementation was carried out. A 55-bp A/T rich (44%) region, which could form a stem-loop structure with a calculated free energy of −49.5 kcal/mol, is present in the 221-bp intergenic region between gap1 and an upstream partial carboxypeptidase gene. Similar gap1-pgk-tpi operons were also found in *S. coelicolor* and *S. avertimilis* (Bentley et al., 2002) (Ikeda et al., 2003). These analyses suggested a promoter could be present in this intergenic region (Strohl, 1992). The recombinant plasmid pSET152/1-95 was constructed by insertion of the 4.0-kb fragment excised from pBS/1-95 into pSET152. The resulting vector was transformed into Gap15-7-30, and the transformants were selected and named Gap15-7-30 (1-95). Three independent transformants were fermented in PES medium. UV and HPLC analyses of imidazole derivatives showed that the yield of clavulanic acid in all three Gap15-7-30 (1-95) strains was consistently reduced during fermentation, whereas the control strain Gap 15-7-30 (pSET152) still produced an undimished level clavulanic acid. Gap15-7-30 (1-95), as shown in FIG. 8b, produced 70% less clavulanic acid than the gap1 mutant at 72 h of fermentation, which is only 25% more than the wild-type strain. These results confirmed that the targeted disruption of gap1 correlated directly with the increased production of clavulanic acid in this mutant.

3.5. Feeding of Gap15-7-30 with Arginine and Glycerol

The availability of arginine is not limiting in wild-type *S. clavuligerus*, so arginine supplementation has no effect on clavulanic acid levels, whereas additions of glycerol resulted in the increased production of clavulanic acid (Chen et al., 2003). To investigate if this is the case in Gap15-7-30, the mutant was fed glycerol or arginine every 24 h at the final concentration of 13.5 mmol and 0.5 mmol, respectively. Surprisingly, no further increase in clavulanic acid production was observed in the cultures fed glycerol, but more than tripled production (422 mg/L, 310%) from cultures fed arginine (FIG. 8a). The effect of arginine started after 60 h of exposure, and clavulanic acid production continuously increased to its maximum at the 192 h of fermentation. Enhanced production was also obtained when Gap15-7-30 was fed both arginine and glycerol, confirming that only arginine was needed to stimulate clavulanic acid production in the mutant. Feeding the mutant with higher concentrations of arginine did not result in additional increases in clavulanic acid production (data not shown).

4. Discussion

Metabolic engineering has become a rational alternative to classical strain improvement for the optimization of metabolite production. The introduction of directed genetic modifications through recombinant DNA technology can be visualized to improve the cellular properties of production strains and result in substantial increases in existing β-lactam antibiotic fermentation processes (Malmberg et al., 1993; Theilgaard et al., 2001). Augmentin® has been available for clinical use for over 20 years and its high effectiveness, safety, and tolerance profiles continue to make it an important agent in the treatment of bacterial infections (White et al., 2004). The development of high-dose formulations of Augmentin®, Augmentin ES-600® and Augmentin XR® (White et al., 2004), requires higher industrial production of clavulanic acid. Increasing the pool size of the rate-limiting precursor is a fundamental approach to strain improvement. This could be achieved by either increasing the gene dosage of key enzymes(s) involved in precursor biosynthesis (Malmberg et al., 1993), or direct feeding of the desired precursor(s) or its closely related derivatives (Chen et al., 2003). We report here a third approach to increasing the intracellular G3P pool by using homologous recombination technology to partially block the downstream portion of the glycolytic pathway that competes with clavulanic acid biosynthesis in *S. clavuligerus*. Thus, the $C_3$-carbohydrate flux that would have normally gone through glycolysis instead would be diverted into clavulanic acid biosynthesis, thus accounting for an overall increase in clavulanic acid yield in the mutant strain. Our findings clearly demonstrate that clavulanic acid production in the gap-disrupted mutant is enhanced up to 282 mg/L (210% of the wild-type strain) in batch cultures in the absence of additives and without changing any components in the fermentation medium. An even higher yield of 422 mg/L (310% of wild-type strain) was achieved in fed-batch cultures in which L-arginine was fed to Gap15-7-30 at low concentration.

4.1. The Glycolytic Pathways in S. clavuligerus

Although the biochemical activities of the glycolytic enzymes have been studied in detail, no information for *S. clavuligerus* has so far been described. Sequence comparisons of GAPDH and PGK from various species have shown that they are among the most-conserved proteins in eubacteria and eukaryotes where large stretches of amino acid residues have changed little or not at all (Jones and Harris, 1972). The genes gap and pgk have been reported to be linked to the triosephosphate isomerase gene (tpi) in many organisms (Bentley et al., 2002) (Ikeda et al., 2003) suggesting that gap1, pgk, and tpi could be also clustered as a tricistronic operon in *S. clavuligerus*.

Although Gap1 and Gap2 have some conserved motifs and amino acid residues that are involved in NAD+−binding and substrate catalysis in GAPDHs, their overall homology is relatively low (25% identity). BLASTP and phylogenetic analyses clearly revealed that Gap1 and Gap2 are homologous to two distinct groups of GAPDHs. The same phenomenon has been observed in Gap1 and Gap2 of *S. coelicolor* (Bentley et al., 2002), indicating the evolutionary distance between these two groups.

4.2. Gap1 is Involved in Metabolism of Glycerol

Unlike gap mutants in most other bacteria in which a glucose assimilation deficiency requires an additional carbon source for survival (Hillman and Fraenkel, 1975; Valverde et al., 1997), the growth of Gap15-7-30 on a variety of media, including PES and PES2 medium (complex) and SA medium (minimal), is similar to the parental strain without any additional carbon source(s). This could be due to in-trans complementation from gap2. The gap2 mutant does not show enhanced clavulanic acid production in either PES or PES2 media, indicating that gap2 might be involved in the metabolism of carbon sources other than glycerol. On the other hand, glycerol can also be metabolized through glycerol hydrogenase, aldehyde dehydrogenase and glycerate kinase to form 2-phosphoglycerate, and then pyruvate (FIG. 1). A gene encoding a putative aldehyde dehydrogenase has been recently identified in *S. clavuligerus*, whose product showed 87% identity to aldehyde dehydrogenases in *S. coelicolor* and *S. avermitilis*, indicating that this glycerol-utilizing pathway is present in *S. clavuligerus*. Thus, in Gap15-7-30 most glycerol is still metabolized through glycolysis, but the buildup of G3P is then channeled to the clavulanic acid pathway. Meanwhile, the alternative glycerol-utilizing pathway produces pyruvate to by-pass the blocked glycolytic pathway.

Gap15-7-30 produces only slightly higher levels of clavulanic acid than the wild-type strain in SA and PES2 media, indicating that, due to the absence of glycerol, the level of carbon flux in the glycolytic pathway is inefficiently low that even the disruption mutant cannot accumulate more G3P. It has been demonstrated that most glycolytic enzymes are substrate inducible (Smith and Chater, 1988). The clavulanic acid production profiles of Gap15-7-30 and Gap2-4-14 in glycerol-containing (PES) and glycerol-absent (PES2 and SA) medium are strongly suggestive that the gap1-pgk-tpi cluster is substrate (glycerol) inducible in *S. clavuligerus*.

4.3. Disruption of Gap1 Relieves the 3-carbon Precursor Limitation

An important finding in this study is that the $C_3$ precursor became saturating after diversion of G3P towards the clavulanic acid biosynthetic pathway, so that feeding the mutant with glycerol no longer resulted in elevated clavulanic acid production. On the contrary, the $C_5$ precursor became rate-limiting, and the administration of arginine apparently alleviated its lack of availability and enhanced clavulanic acid production. This indicates that the increased pool of G3P is so significant that even the very effective urea cycle and a paralogous gene encoding OAT in the clavulanic acid gene cluster (Kershaw et al., 2002) can not provide sufficient arginine to fully supply the Gap 15-7-30 mutant. When glycerol and arginine were both fed, the production of clavulanic acid was close to that with added arginine alone. This might be because the increased intracellular concentrations of $C_3$ and $C_5$ precursors have saturated CEAS, the first dedicated biosynthetic enzyme of the pathway, and introduced a new bottleneck downstream in the overall pathway to clavulanic acid.

4.4. Additional Exemplary Applications in Industry

Because mutants generated by double-crossover through homologous recombination are genetically stable, the metabolic switch is permanent. Industrial production of clavulanic acid uses a similar fermentation medium that also contains glycerol (Elander, 2003), suggesting that our technology could be easily applied for strain/method improvement. Clavulanic acid and the antipodal clavams use the same primary metabolic precursors and share the early part of the biosynthetic pathway up to the common intermediate clavaminic acid (Townsend, 2002). Thus, some of the increased G3P pool likely flows into the clavam pathway and would be anticipated to result in an increased yield of clavams. It has been shown that disruption of clavam biosynthesis has a positive effect on clavulanic acid production (Mosher et al., 1999; Paradkar et al., 2001). Therefore, the yield of clavulanic acid could be further improved if clavam biosynthesis were also blocked in Gap15-7-30. This approach would in addition eliminate clavam contamination so that the subsequent extraction and purification of clavulanic acid from the fermentation broth would be simplified.

Improved production of secondary metabolites involves significant changes in precursor flux, energy, and cofactors from primary to secondary metabolism (Drew and Demain, 1977). Based on understanding the biosynthetic pathway characterized so far, the increased clavulanic acid productivity in Gap15-7-30 would raise the competition for arginine, ATP (β-LS), α-KG (CS2), and NADPH (CAD) between primary and secondary metabolism, and introduce new metabolic bottlenecks.

REFERENCES

Aoki, H., Y. Kubochi, E. Iguchi, and H. Imanaka (1976) Nocardicin A, a new monocyclic β-lactam antibiotic. I. Discovery, isolation and characterization. J. Antibiot. 29: 492-500. Baltz, R. H. (1998) New genetic methods to improve secondary metabolite production in *Streptomyces*. J. Ind. Microbiol. Biot. 20: 360-363.

Baltz, R. H. (2001) Genetic methods and strategies for secondary metabolite yield improvement in actinomycetes. Antonie van Leeuwenhoek 79: 251-259.

Bascaran, V., Hardisson, C., and Brana, A. F. (1989) Isolation and characterization of nitrogen-deregulated mutants of *Streptomyce clavuligerus*. J. Gen. Microbiol. 135: 2475-2482.

Bentley, S. D., Chater, K. F., Cerdeno-Tarraga, A. M., Challis, G. L., Thomson, N. R., James, K. D., Harris, D. E., Quail, M. A., Kieser, H., Harper, D., Bateman, A., Brown, S., Chandra, G., Chen, C. W., Collins, M., Cronin, A., Fraser, A., Goble, A., Hidalgo, J., Hornsby, T., Howarth, S., Huang, C. H., Kieser, T., Larke, L., Murphy, L., Oliver, K., O'Neil, S., Rabbinowitsch, E., Rajandream, M. A., Rutherford, K., Rutter, S., Seeger, K., Saunders, D., Sharp, S., Squares, R., Squares, S., Taylor, K., Warren, T., Wietzorrek, A., Woodward, J., Barrell, B. G., Parkhill, J., and Hopwood, D. A. (2002) Complete genome sequence of the model actinomycete *Streptomyces coelicolor* A3(2). Nature 417: 141-147.

Bierman, M., R. Logan, K. O'Brien, E. T. Seno, R. Nagaraja Rao, and B. E. Schoner (1992) Plasmid cloning vectors for the conjugal transfer of DNA from *Escherichia coli* to *Streptomyces* spp. Gene 116: 43-49.

Bird, A. E., J. M. Bellis, and B. C. Gasson (1982) Spectrophotometric assay of clavulanic acid by reaction with imidazole. Analyst 107: 1241-1245.

Brown, A. G., Butterworth, D., Cole, M., Handcomb, G., Hood, J. D., Reading, C., and Rolinson, C. N. (1976) Naturally occurring β-lactamase inhibitors without antibacterial activity. J. Antibiot. 29: 668-669.

Chen, K. C., Lin, Y. H., Tsai, C. M., Hsieh, C. H., and Houng, J. Y. (2002) Optimization of glycerol feeding for clavulanic acid production by *Streptomyces clavuligerus* with glycerol feeding. Biotechnol. Lett. 24: 455-458.

Chen, K. C., Lin, Y. H., Wu, J. Y., and Hwang, S. C. J. (2003) Enhancement of clavulanic acid production in *Streptomyces clavuligerus* with ornithine feeding. Enzyme Microb. Technol. 32: 152-156.

Drew, S. W., and Demain, A. L. (1977) Effect of primary metabolism on secondary metabolism. Annu. Rev. Microbiol. 31: 343-356.

Eisenriech, W., A. Bacher, D. Arigoni an dF. Rohdich (2004) Biosynthesis of isoprenoids via the non-mevalonate pathway. CMLS Cell. Mol. Life Sci. 61: 1401-1426.

Elander, R. P. (2003) Industrial production of β-lactam antibiotics. Appl. Microbiol. Biotechnol. 61: 385-392.

Hillman, J. D., and Fraenkel, D. G. (1975) Glyceraldehyde-3-phosphate dehydrogenase mutants of *Escherichia coli*. J. Bacteriol. 122: 1175-1179.

Hong, S. J., Seong, K. Y., Sohn, W. M., and Song, K. Y. (2000) Molecular cloning and immunological characterization of phosphoglycerate kinase from *Clonorchis sinensis*. Mol. Biochem. Parasitol. 108: 207-216.

Howarth, T. T., Brown, A. G., and King, T. J. (1976) Clavulanic acid, a novel b-lactam isolated from *Streptomyces clavuligerus*: X-ray crystal structure analysis. J. Chem. Soc. Chem. Commun.: 266-267.

Ikeda, H., Ishikawa, J., Hanamoto, A., Shinose, M., Kikuchi, H., Shiba, T., Sakaki, Y., Hattori, M., and Omura, S. (2003) Complete genome sequence and comparative analysis of the industrial microorganism *Streptomyces avermitilis*. Nat. Biotechnol. 21: 526-531.

Ishikawa, J., and K. Hotta (1999) FramePlot: a new implementation of the Frame analysis for predicting protein-coding regions in bacterial DNA with a high G+C content. FEMS Microbiol. Lett. 174: 251-253.

Ives, P. R., and Bushell, M. E. (1997) Manipulation of the physiology of clavulanic acid production in *Streptomyces clavuligerus*. Microbiology 143: 3573-3579.

Jensen, S. E. and Paradkar, A. S. (1999) Biosynthesis and Molecular Genetics of Clavulanic Acid. Antonie van Leeuwenhoek 75: 125-133.

Jones, J. M. T., and Harris, J. I. (1972) Glyceraldehyde-3-phosphate dehydrogenase: amino acid sequence of enzyme from baker's yeast. FEBS Lett. 22: 185-189.

Kershaw, N. J., McNaughton, H. J., Hewitson, K. S., Hernandez, H., Griffin, J., Hughes, C., Greaves, P., Barton, B., Robinson, C. V., and Schofield, C. J. (2002) ORF6 from the clavulanic acid gene cluster of *Streptomyces clavuligerus* has ornithine acetyltransferase activity. Eur. J. Biochem. 269: 2052-2059.

Khaleeli, N., Li, R. F., and Townsend, C. A. (1999) Origin of the β-lactam carbons in clavulanic acid from a unusual thiamine pyrophosphate-mediated reaction. J. Am. Chem. Soc. 121: 9223-9224.

Kieser, H. M., Bibb, M. J., Buttner, M. J., Chater, K. F., and Hopwood, D. A. (2000) Practical *Streptomyces* Genetics. Norwich, United Kingdom: The John Innes Foundation.

Kirk, S., Avignone-Rossa, C. A., and Bushell, M. E. (2000) Growth limiting substrate affects antibiotic production and associated metabolic fluxes in *Streptomyces clavuligerus*. Biotechnol. Lett. 22: 1803-1809.

Li, R. F., Khaleeli, N., and Townsend, C. A. (2000) Expansion of the clavulanic acid gene cluster: identification and in vivo functional analysis of three new genes required for biosynthesis of clavulanic acid by *Streptomyces clavuligerus*. J. Bacteriol. 182: 4087-4095.

Malmberg, L. H., Hu, W. S., and Sherman, D. H. (1993) Precursor flux control through targeted chromosomal insertion of the lysine ∈-aminotransferase (lat) gene in cephamycin C biosynthesis. J. Bacteriol. 175: 6916-6924.

Mateos, M. I., and Serrano, A. (1992) Occurrence of phosphorylating and non-phosphorylating NADP+−dependent glyceraldehyde-3-phosphate dehydrogenases in photosynthetic organisms. Plant Sci. 84: 163-170.

May, B. P. (1998) Southern hybridization in shampoo. BioTechniques 25: 582.

Mosher, R. H., Paradkar, A. S., Anders, C., Barton, B., and Jensen, S. E. (1999) Genes specific for the biosynthesis of clavam metabolites antipodal to clavulanic acid are clustered with the gene for clavaminate synthase 1 in *Streptomyces clavuligerus*. Antimicrob. Agents Chemother. 43: 1215-1224.

Nielsen, J. (1997) Physiological engineering aspects of *Penicillium chrysogenum*. In World Scientific Singapore.

Paradkar, A. S., and Jensen, S. E. (1995) Functional analysis of the gene encoding the clavaminate synthase 2 isoenzyme involved in clavulanic acid biosynthesis in *Streptomyces clavuligerus*. J. Bacteriol. 177: 1307-1314.

Paradkar, A. S., Aidoo, K. A., and Jensen, S. E. (1998) A pathway-specific transcriptional activitor regulates late steps of clavulanic acid biosynthesis in *Streptomyces clavuligerus*. Mol. Microbiol. 27: 831-843.

Paradkar, A. S., Mosher, R. H., Anders, C., Griffin, A., Griffin, J., Hughes, C., Greaves, P., Barton, B., and Jensen, S. E. (2001) Applications of gene replacement technology to *Streptomyces clavuligerus* strain development for clavulanic acid production. Appl. Environ. Microbiol. 67: 2292-2297.

Perez-Llarena, F. J., Liras, P., Rodriguez-Garcia, A., and Martin, J. F. (1997) A regulatory gene (ccaR) required for cephamycin and clavulanic acid production in *Streptomyces clavuligerus*: amplification results in overproduction of both β-lactam compounds. J. Bacteriol. 179: 2053-2059.

Perez-Redondo, R., Rodriguez-Garcia, A., Martin, J. F., and Liras, P. (1998) The claR gene of *Streptomyces clavuligerus*, encoding a LysR-type regulatory protein controlling clavulanic acid biosynthesis, is linked to the clavulanate-9-aldehyde reductase (car) gene. Gene 211: 311-321.

Perez-Redondo, R., Rodriguez-Garcia, A., Martin, J. F., and Liras, P. (1999) Deletion of the pyc gene blocks clavulanic acid biosynthesis except in glycerol-containing medium: evdience for two dofferent genes in formation of the C3 unit. J. Bacteriol. 181: 6922-6928.

Pruess, D. L., and Kellett, M. (1983) Ro-22-5417, a new clavam antibiotic from *Streptomyces clavuligerus*. I. Discovery and biological activity. J. Antibiot. 36: 208-212.

Reading, E., and Cole (1977) Clavulanic acid: a beta-lactamase inhibitor from *Streptomyces clavuligerus*. Antimicrob. Agents Chemother. 11: 852-857.

Romero, J., P. Liras, and J. F. Martin (1984) Dissociation of cephamycin and clavulanic acid biosynthesis in *Streptomyces clavuligerus*. Appl. Microbiol. Biotechnol. 20: 318-325.

Romero, J., Liras, P., and Martin, J. F. (1986) Utilisation of ornithine and arginine as specific precursors of clavulanic acid. Appl. Environ. Microbiol. 52: 892-897.

Rose, T. M., Schultz, E. R., Henikoff, J. G., Pietrokovski, S., McCallum, C. M., and Henikoff, S. (1998) Consensus-degenerate hybrid oligonucleotide primers for amplification of distantly related sequences. Nucleic Acid Res. 26: 1628-1635.

Sambrook, J., Fritsch, E. F., and Maniatis, T. (1989) Molecular cloning: a laboratory manual, 2nd ed. Cold Spring Harbor, N.Y. Cold Spring Harbor Laboratory Press.

Skarzynski, T., Moody, P. C. E., and Wonacott, A. J. (1987) Structure of hologlyceraldehyde-3-phosphate dehydrogenase from *Bacillus stearothermophilus* at 1.8A resolution. J. Mol. Biol. 193: 171-187.

Smith, C. P., and Chater, K. F. (1988) Structure and regulation of controlling sequences for the *Streptomyces coelicolor* glycerol operon. J. Mol. Biol. 204: 569-580.

Strohl, W. R. (1992) Compilation and analysis of DNA sequences associated with apprant streptomycete promoters. Nucleic Acid Res. 20: 961-974.

Theilgaard, H. B. A., van den Berg, M., Mulder, C., Bovenberg, R. A. L., and Nielsen, J. (2001) Quantitative analysis of *Penicillium chrysogenum* Wis54-1255 transformants over-expressed in the penicillin biosynthetic genes. Biotechnol. Bioeng. 72: 379-388.

Townsend, C. A. (2002) New reaction in clavulanic acid biosynthesis. Curr. Opin. Chem. Biol. 6: 583-589.

Valentine, B. P., Bailey, A., Doherty, J., Morris, S., Elson, S. W., and Baggaley, K. H. (1993) Evidence that arginine is a later metabolic intermediate than ornithine in the biosynthesis of clavulanic acid by *Streptomyces clavuligerus*. J. Chem. Soc. Chem. Common. 1993: 1210-1211.

Valverde, F., losada, M., and Serrano, A. (1997) Functional complementation of an *Escherichia coli* gap mutant supports an amphibolic role for NAD(P)H-dependent glyceraldehyde-3-phosphate dehydrogenase of *Synechocystis* sp. strain PCC 6803. J. Bacteriol. 179: 4513-4522.

Vara, J., Lewandowska-Skarbek, M., Wang, Y. G., Donadio, S., and Hutchinson, C. R. (1989) Cloning of gene governing the deoxysuger portion of the erythromycin biosynthesis pathway in *Saccharopolyspora erythraea* (*Streptomyces erythreus*). J. Bacteriol. 171: 5872-5881. White, A. R., Kaye, C., Poupard, J., Pypstra, R., Woodnutt, G., and Wynne, B. (2004) Augmentin (amoxicillin/clavulanate) in the treatment of community-acquired respiratory tract infection: a review of the continuing development of an innovative antimicrobial agent. J. Antimicrobiol. Chemother. 53: i3-i20.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. *Streptomyces clavuligerus* genetically modified such that a nucleic acid sequence encoding the glyceraldehyde-3-phosphate dehydrogenase (GAPDH) of SEQ ID NO: 43 is deleted or mutated so that GAPDH activity is missing or reduced, or progeny thereof.

2. The *Streptomyces clavuligerus* of claim 1, wherein said nucleic acid sequence encoding a GAPDH enzyme is SEQ ID NO: 50.

* * * * *

SEQUENCE LISTING

```
<160> NUMBER OF SEQ ID NOS: 59

<210> SEQ ID NO 1
<211> LENGTH: 12
<212> TYPE: PRT
<213> ORGANISM: Streptomyces coelicolor

<400> SEQUENCE: 1

His His Val Ile Ser Asn Ala Ser Cys Thr Thr Asn
1               5                   10

<210> SEQ ID NO 2
<211> LENGTH: 10
<212> TYPE: PRT
<213> ORGANISM: Streptomyces coelicolor

<400> SEQUENCE: 2

Lys Asp Leu Arg Arg Ala Arg Ala Ala Ala
1               5                   10

<210> SEQ ID NO 3
<211> LENGTH: 10
```

<212> TYPE: PRT
<213> ORGANISM: Streptomyces coelicolor

<400> SEQUENCE: 3

Trp Tyr Asp Asn Glu Trp Gly Tyr Ser Asn
1               5                   10

<210> SEQ ID NO 4
<211> LENGTH: 12
<212> TYPE: PRT
<213> ORGANISM: Thermoanaerobacter tengcongensis

<400> SEQUENCE: 4

His His Val Ile Ser Asn Ala Ser Cys Thr Thr Asn
1               5                   10

<210> SEQ ID NO 5
<211> LENGTH: 10
<212> TYPE: PRT
<213> ORGANISM: Thermoanaerobacter tengcongensis

<400> SEQUENCE: 5

Ser Asp Leu Arg Arg Ala Arg Ala Ala Ala
1               5                   10

<210> SEQ ID NO 6
<211> LENGTH: 10
<212> TYPE: PRT
<213> ORGANISM: Thermoanaerobacter tengcongensis

<400> SEQUENCE: 6

Trp Tyr Asp Asn Glu Trp Gly Tyr Ser Asn
1               5                   10

<210> SEQ ID NO 7
<211> LENGTH: 12
<212> TYPE: PRT
<213> ORGANISM: Thermobifida fusca

<400> SEQUENCE: 7

His His Ile Leu Ser Asn Ala Ser Cys Thr Thr Asn
1               5                   10

<210> SEQ ID NO 8
<211> LENGTH: 10
<212> TYPE: PRT
<213> ORGANISM: Thermobifide fusca

<400> SEQUENCE: 8

Lys Asp Leu Arg Arg Ala Arg Ala Ala Ala
1               5                   10

<210> SEQ ID NO 9
<211> LENGTH: 10
<212> TYPE: PRT
<213> ORGANISM: Thermobifida fusca

<400> SEQUENCE: 9

Trp Tyr Asp Asn Glu Trp Gly Tyr Ser Asn
1               5                   10

<210> SEQ ID NO 10
<211> LENGTH: 12
<212> TYPE: PRT
<213> ORGANISM: Streptomyces aureofaciens

```
<400> SEQUENCE: 10

His Thr Ile Val Ser Asn Ala Ser Cys Thr Thr Asn
1               5                  10

<210> SEQ ID NO 11
<211> LENGTH: 10
<212> TYPE: PRT
<213> ORGANISM: Streptomyces aureofaciens

<400> SEQUENCE: 11

Arg Asp Pro Arg Arg Ala Arg Ala Ala Ala
1               5                  10

<210> SEQ ID NO 12
<211> LENGTH: 10
<212> TYPE: PRT
<213> ORGANISM: Streptomyces aureofaciens

<400> SEQUENCE: 12

Trp Tyr Asp Asn Glu Trp Gly Phe Ser Asn
1               5                  10

<210> SEQ ID NO 13
<211> LENGTH: 12
<212> TYPE: PRT
<213> ORGANISM: Mycobacterium tuberculosis

<400> SEQUENCE: 13

Gln Asn Ile Ile Ser Asn Ala Ser Cys Thr Thr Asn
1               5                  10

<210> SEQ ID NO 14
<211> LENGTH: 10
<212> TYPE: PRT
<213> ORGANISM: Mycobacterium tuberculosis

<400> SEQUENCE: 14

Lys Asp Leu Arg Arg Ala Arg Ala Ala Ala
1               5                  10

<210> SEQ ID NO 15
<211> LENGTH: 10
<212> TYPE: PRT
<213> ORGANISM: Mycobacterium tuberculosis

<400> SEQUENCE: 15

Trp Tyr Asp Asn Glu Trp Gly Tyr Ser Asn
1               5                  10

<210> SEQ ID NO 16
<211> LENGTH: 12
<212> TYPE: PRT
<213> ORGANISM: Bacillus megaterium

<400> SEQUENCE: 16

His Asn Val Ile Ser Asn Ala Ser Cys Thr Thr Asn
1               5                  10

<210> SEQ ID NO 17
<211> LENGTH: 10
<212> TYPE: PRT
<213> ORGANISM: Bacillus megaterium

<400> SEQUENCE: 17
```

```
Lys Asp Tyr Arg Arg Ala Arg Ala Ala Ala
1               5                   10
```

<210> SEQ ID NO 18
<211> LENGTH: 10
<212> TYPE: PRT
<213> ORGANISM: Bacillus megaterium

<400> SEQUENCE: 18

```
Trp Tyr Asp Asn Glu Ser Gly Tyr Ser Asn
1               5                   10
```

<210> SEQ ID NO 19
<211> LENGTH: 12
<212> TYPE: PRT
<213> ORGANISM: Mycobacterium avium

<400> SEQUENCE: 19

```
Gln Asn Ile Ile Ser Asn Ala Ser Cys Thr Thr Asn
1               5                   10
```

<210> SEQ ID NO 20
<211> LENGTH: 10
<212> TYPE: PRT
<213> ORGANISM: Mycobacterium avium

<400> SEQUENCE: 20

```
Lys Asp Leu Arg Arg Ala Arg Ala Ala Ala
1               5                   10
```

<210> SEQ ID NO 21
<211> LENGTH: 10
<212> TYPE: PRT
<213> ORGANISM: Mycobacterium avium

<400> SEQUENCE: 21

```
Trp Tyr Asp Asn Glu Trp Gly Tyr Ser Asn
1               5                   10
```

<210> SEQ ID NO 22
<211> LENGTH: 12
<212> TYPE: PRT
<213> ORGANISM: Streptomyces arenae

<400> SEQUENCE: 22

```
His Thr Ile Ile Ser Asn Ala Ser Cys Thr Thr Asn
1               5                   10
```

<210> SEQ ID NO 23
<211> LENGTH: 10
<212> TYPE: PRT
<213> ORGANISM: Streptomyces arenae

<400> SEQUENCE: 23

```
Lys Asp Leu Arg Arg Ala Arg Ala Ala Ala
1               5                   10
```

<210> SEQ ID NO 24
<211> LENGTH: 10
<212> TYPE: PRT
<213> ORGANISM: Streptomyces arenae

<400> SEQUENCE: 24

```
Trp Tyr Asp Asn Glu Trp Gly Tyr Ser Asn
```

```
<210> SEQ ID NO 25
<211> LENGTH: 12
<212> TYPE: PRT
<213> ORGANISM: Oceanobacillus iheyensis

<400> SEQUENCE: 25

His Asn Val Ile Ser Asn Ala Ser Cys Thr Thr Asn
1               5                   10

<210> SEQ ID NO 26
<211> LENGTH: 10
<212> TYPE: PRT
<213> ORGANISM: Oceanobacillus iheyensis

<400> SEQUENCE: 26

Lys Asp Tyr Arg Arg Ala Arg Ala Ala Ala
1               5                   10

<210> SEQ ID NO 27
<211> LENGTH: 10
<212> TYPE: PRT
<213> ORGANISM: Oceanobacillus iheyensis

<400> SEQUENCE: 27

Trp Tyr Asp Asn Glu Met Gly Tyr Ser Ala
1               5                   10

<210> SEQ ID NO 28
<211> LENGTH: 12
<212> TYPE: PRT
<213> ORGANISM: Streptomyces avermitilis

<400> SEQUENCE: 28

His Asn Val Ile Ser Asn Ala Ser Cys Thr Thr Asn
1               5                   10

<210> SEQ ID NO 29
<211> LENGTH: 10
<212> TYPE: PRT
<213> ORGANISM: Streptomyces avermitilis

<400> SEQUENCE: 29

Lys Asp Leu Arg Arg Ala Arg Ala Ala Ala
1               5                   10

<210> SEQ ID NO 30
<211> LENGTH: 10
<212> TYPE: PRT
<213> ORGANISM: Streptomyces avermitilis

<400> SEQUENCE: 30

Trp Tyr Asp Asn Glu Trp Gly Tyr Ser Asn
1               5                   10

<210> SEQ ID NO 31
<211> LENGTH: 12
<212> TYPE: PRT
<213> ORGANISM: Clostridium tetani

<400> SEQUENCE: 31

His Asn Ile Ile Ser Asn Ala Ser Cys Thr Thr Asn
1               5                   10
```

<210> SEQ ID NO 32
<211> LENGTH: 10
<212> TYPE: PRT
<213> ORGANISM: Clostridium tetani

<400> SEQUENCE: 32

Lys Asp Leu Arg Arg Ala Arg Ala Ala Ala
1               5                   10

<210> SEQ ID NO 33
<211> LENGTH: 10
<212> TYPE: PRT
<213> ORGANISM: Clostridium tetani

<400> SEQUENCE: 33

Trp Tyr Asp Asn Glu Trp Gly Tyr Ser Thr
1               5                   10

<210> SEQ ID NO 34
<211> LENGTH: 12
<212> TYPE: PRT
<213> ORGANISM: Bacillus cereus

<400> SEQUENCE: 34

His Asn Val Val Ser Asn Ala Ser Cys Thr Thr Asn
1               5                   10

<210> SEQ ID NO 35
<211> LENGTH: 10
<212> TYPE: PRT
<213> ORGANISM: Bacillus cereus

<400> SEQUENCE: 35

Lys Asp Leu Arg Arg Ala Arg Ala Ala Ala
1               5                   10

<210> SEQ ID NO 36
<211> LENGTH: 10
<212> TYPE: PRT
<213> ORGANISM: Bacillus cereus

<400> SEQUENCE: 36

Trp Tyr Asp Asn Glu Thr Gly Tyr Ser Asn
1               5                   10

<210> SEQ ID NO 37
<211> LENGTH: 29
<212> TYPE: DNA
<213> ORGANISM: Artificial
<220> FEATURE:
<223> OTHER INFORMATION: synthetic oligonucleotide primer designed for
      the M1 motif; N is A, T, G or C; Y is C or T
<220> FEATURE:
<221> NAME/KEY: misc_feature
<222> LOCATION: (21)..(21)
<223> OTHER INFORMATION: n may be c or t
<220> FEATURE:
<221> NAME/KEY: misc_feature
<222> LOCATION: (24)..(24)
<223> OTHER INFORMATION: n may be a, t, c or g
<220> FEATURE:
<221> NAME/KEY: misc_feature
<222> LOCATION: (27)..(27)
<223> OTHER INFORMATION: n may be a, t, c or g

<400> SEQUENCE: 37
atcatctcca acgcctcctg nacnacnaa                                          29

```
<210> SEQ ID NO 38
<211> LENGTH: 9
<212> TYPE: PRT
<213> ORGANISM: Artificial
<220> FEATURE:
<223> OTHER INFORMATION: M1 consensus motif

<400> SEQUENCE: 38

Ile Ile Ser Asn Ala Ser Cys Thr Thr
1               5

<210> SEQ ID NO 39
<211> LENGTH: 26
<212> TYPE: DNA
<213> ORGANISM: Artificial
<220> FEATURE:
<223> OTHER INFORMATION: Synthetic oligonucleotide primer for M2 motif;
      M is A or C; N is A, T, G, or C
<220> FEATURE:
<221> NAME/KEY: misc_feature
<222> LOCATION: (16)..(16)
<223> OTHER INFORMATION: n is a or c
<220> FEATURE:
<221> NAME/KEY: misc_feature
<222> LOCATION: (18)..(18)
<223> OTHER INFORMATION: n is a, t, g, or c
<220> FEATURE:
<221> NAME/KEY: misc_feature
<222> LOCATION: (21)..(21)
<223> OTHER INFORMATION: n is a, t, g, or c
<220> FEATURE:
<221> NAME/KEY: misc_feature
<222> LOCATION: (24)..(24)
<223> OTHER INFORMATION: n is a, t, g, or c

<400> SEQUENCE: 39
gacctccgcc gcgccngngc ngcngc                                          26

<210> SEQ ID NO 40
<211> LENGTH: 8
<212> TYPE: PRT
<213> ORGANISM: Artificial
<220> FEATURE:
<223> OTHER INFORMATION: M2 consensus motif

<400> SEQUENCE: 40

Asp Leu Arg Arg Ala Arg Ala Ala
1               5

<210> SEQ ID NO 41
<211> LENGTH: 28
<212> TYPE: DNA
<213> ORGANISM: Artificial
<220> FEATURE:
<223> OTHER INFORMATION: Synthetic ligonucleotide primer for M3 motif;
      R is A or G
<220> FEATURE:
<221> NAME/KEY: misc_feature
<222> LOCATION: (20)..(20)
<223> OTHER INFORMATION: n may be a or g
<220> FEATURE:
<221> NAME/KEY: misc_feature
<222> LOCATION: (23)..(23)
<223> OTHER INFORMATION: n may be a or g

<400> SEQUENCE: 41
tggagtagcc ccactcgttn tcntacca                                        28

<210> SEQ ID NO 42
```

```
<211> LENGTH: 9
<212> TYPE: PRT
<213> ORGANISM: Artificial
<220> FEATURE:
<223> OTHER INFORMATION: M3 consensus motif

<400> SEQUENCE: 42

Ser Tyr Gly Trp Glu Asn Asp Tyr Trp
1               5

<210> SEQ ID NO 43
<211> LENGTH: 335
<212> TYPE: PRT
<213> ORGANISM: Streptomyces clavuligerus

<400> SEQUENCE: 43

Met Thr Ile Arg Val Gly Ile Asn Gly Phe Gly Arg Ile Gly Arg Asn
1               5                   10                  15

Tyr Phe Arg Ala Leu Leu Glu Gln Gly Ala Asp Ile Glu Ile Val Ala
            20                  25                  30

Val Asn Asp Leu Gly Asp Thr Ala Thr Thr Ala His Leu Leu Lys Tyr
        35                  40                  45

Asp Thr Ile Leu Gly Arg Leu Lys Ala Glu Val Thr His Thr Ala Asp
    50                  55                  60

Thr Ile Thr Val Asp Gly His Thr Ile Lys Val Leu Ser Glu Arg Asn
65                  70                  75                  80

Pro Ala Asp Ile Pro Trp Gly Glu Leu Gly Val Asp Ile Val Ile Glu
                85                  90                  95

Ser Thr Gly Ile Phe Thr Lys Lys Ala Asp Ala Glu Lys His Leu Ala
            100                 105                 110

Gly Gly Ala Lys Lys Val Leu Ile Ser Ala Pro Ala Lys Asp Glu Asp
        115                 120                 125

Ile Thr Leu Val Met Gly Val Asn Gln Asp Thr Tyr Asp Pro Ala Gln
    130                 135                 140

His His Val Ile Ser Asn Ala Ser Cys Thr Thr Asn Cys Val Ala Pro
145                 150                 155                 160

Met Ala Lys Val Leu Asp Glu Asn Phe Gly Ile Val Arg Gly Leu Met
                165                 170                 175

Thr Thr Val His Ala Tyr Thr Asn Asp Gln Arg Ile Leu Asp Phe Pro
            180                 185                 190

His Ser Asp Leu Arg Arg Ala Arg Ala Ala Glu Asn Ile Ile Pro
        195                 200                 205

Thr Thr Thr Gly Ala Ala Lys Ala Thr Ala Leu Val Leu Pro Gln Leu
    210                 215                 220

Lys Gly Lys Leu Asp Gly Ile Ala Met Arg Val Pro Val Pro Thr Gly
225                 230                 235                 240

Ser Ala Thr Asp Leu Val Val Glu Leu Ser Arg Glu Val Thr Lys Asp
                245                 250                 255

Glu Val Asn Ala Ala Phe Lys Lys Ala Ala Glu Gly Glu Leu Gln Gly
            260                 265                 270

Ile Leu Ser Tyr Thr Glu Asp Pro Ile Val Ser Ser Asp Ile Val Gly
        275                 280                 285

Asp Pro Ala Ser Cys Thr Phe Asp Ser Ser Leu Thr Met Val Gln Glu
    290                 295                 300

Gly Asn Ser Val Lys Ile Leu Gly Trp Tyr Asp Asn Glu Trp Gly Tyr
305                 310                 315                 320
```

Ser Asn Arg Leu Val Asp Leu Thr Val Phe Val Gly Glu Gln Leu
            325                 330                 335

<210> SEQ ID NO 44
<211> LENGTH: 333
<212> TYPE: PRT
<213> ORGANISM: Streptomyces arenae

<400> SEQUENCE: 44

Met Thr Val Arg Ile Gly Ile Asn Gly Phe Gly Arg Ile Gly Arg Asn
1               5                   10                  15

Val Phe Arg Ala Ala Ala Arg Ser Ser Glu Leu Glu Ile Val Ala
            20                  25                  30

Val Asn Asp Leu Gly Asp Val Pro Thr Met Ala His Leu Leu Ala Tyr
            35                  40                  45

Asp Ser Ile Leu Gly Arg Phe Pro Glu Glu Val Thr Ala Glu Pro Gly
        50                  55                  60

Ala Ile Arg Val Gly Asp Arg Thr Ile Lys Val Leu Ala Glu Arg Asp
65                  70                  75                  80

Pro Gly Ala Leu Pro Trp Gly Asp Leu Gly Val Asp Ile Val Ile Glu
                85                  90                  95

Ser Thr Gly Ile Phe Thr Asp Ala Ala Lys Ala Arg Ser His Val Asp
            100                 105                 110

Gly Gly Ala Lys Lys Val Ile Ile Ala Ala Pro Ala Ser Gly Glu Asp
            115                 120                 125

Phe Thr Val Val Leu Gly Val Asn Asp Gly Asp Tyr Asp Pro Glu Arg
        130                 135                 140

His Thr Ile Ile Ser Asn Ala Ser Cys Thr Thr Asn Cys Leu Gly Val
145                 150                 155                 160

Leu Ala Lys Val Leu His Asp Ala Val Gly Ile Asp Ser Gly Met Met
                165                 170                 175

Thr Thr Val His Ala Tyr Thr Gln Asp Gln Asn Leu Gln Asp Ala Pro
            180                 185                 190

His Lys Asp Leu Arg Arg Ala Arg Ala Ala Leu Asn Ile Val Pro
            195                 200                 205

Thr Ser Ser Gly Ala Ala Lys Ala Ile Gly Leu Val Leu Pro Glu Leu
        210                 215                 220

Ala Gly Arg Leu Asp Ala Phe Ala Leu Arg Val Pro Val Pro Thr Gly
225                 230                 235                 240

Ser Val Thr Asp Leu Thr Val Thr Thr Arg Arg Gly Thr Ser Val Glu
                245                 250                 255

Glu Val Lys Glu Ala Tyr Ala Ala Ala Ala Ser Gly Pro Tyr Lys Gly
            260                 265                 270

Leu Leu Ser Tyr Val Asp Ala Pro Leu Val Ser Thr Asp Ile Val Gly
        275                 280                 285

Asp Pro Ala Ser Leu Phe Asp Ala Gly Leu Thr Arg Val Cys Gly Pro
            290                 295                 300

Gln Val Lys Val Val Gly Trp Tyr Asp Asn Glu Trp Gly Tyr Ser Asn
305                 310                 315                 320

Arg Leu Ile Asp Leu Ala Thr Leu Ile Gly Ser Ser Leu
                325                 330

<210> SEQ ID NO 45
<211> LENGTH: 333
<212> TYPE: PRT
<213> ORGANISM: Streptomyces aureofaciens

<400> SEQUENCE: 45

| | | | | | | | | | | | | | | |
|---|---|---|---|---|---|---|---|---|---|---|---|---|---|---|
|Met|Thr|Ile|Arg|Ile|Ala|Ile|Asn|Gly|Phe|Gly|Arg|Ile|Gly|Arg|Asn|
|1| | | |5| | | | |10| | | | |15| |

Val Leu Arg Ala Leu Leu Glu Arg Asp Ser Asp Leu Asp Val Val Ala
          20               25              30

Val Asn Asp Leu Thr Glu Pro Ala Thr Leu Ala Arg Leu Leu Ala Tyr
          35               40              45

Asp Thr Thr Ser Gly Arg Leu Gly Arg Pro Val Thr Val Glu Gly Asn
    50               55              60

Val Leu Val Val Asp Gly Arg Arg Ile Thr Val Thr Ala Glu Arg Glu
65               70              75              80

Pro Ala Asn Leu Pro Trp Ala Glu Leu Gly Val Asp Ile Val Leu Glu
          85               90              95

Ala Thr Gly Arg Phe Thr Ser Ala Lys Ala Ala Arg Ala His Leu Asp
         100            105            110

Ala Gly Ala Lys Lys Val Leu Val Ser Ala Pro Ala Asp Gly Ala Asp
         115            120            125

Ile Thr Leu Ala Phe Gly Val Asn Thr Asp Ala Tyr Asp Pro Asp Leu
         130            135            140

His Thr Ile Val Ser Asn Ala Ser Cys Thr Thr Asn Ala Leu Ala Pro
145              150             155            160

Leu Ala Lys Val Leu Asp Asp Leu Ala Gly Ile Glu His Gly Phe Met
         165            170            175

Thr Thr Val His Ala Tyr Thr Gln Glu Gln Asn Leu Gln Asp Gly Pro
         180            185            190

His Arg Asp Pro Arg Arg Ala Arg Ala Ala Ala Val Asn Ile Val Pro
         195            200            205

Thr Thr Thr Gly Ala Ala Lys Ala Ile Gly Leu Val Leu Pro Asn Leu
         210            215            220

Asp Gly Lys Leu Ser Gly Asp Ser Ile Arg Val Pro Val Pro Val Gly
225              230             235            240

Ser Ile Val Glu Leu Asn Thr Thr Val Ala Arg Asp Val Thr Arg Asp
         245            250            255

Glu Val Leu Asp Ala Tyr Arg Ala Ala Ala Gln Gly Pro Leu Ala Gly
         260            265            270

Val Leu Glu Tyr Ser Glu Asp Pro Leu Val Ser Ser Asp Ile Thr Gly
         275            280            285

Asn Pro Ala Ser Ser Ile Phe Asp Ser Glu Leu Thr Arg Val Asp Gly
         290            295            300

Arg His Ile Lys Val Val Ala Trp Tyr Asp Asn Glu Trp Gly Phe Ser
305              310             315            320

Asn Arg Val Ile Asp Thr Leu Gln Leu Leu Ala Ala Arg
         325            330

<210> SEQ ID NO 46
<211> LENGTH: 336
<212> TYPE: PRT
<213> ORGANISM: Streptomyces coelicolor

<400> SEQUENCE: 46

Met Thr Ile Arg Val Gly Ile Asn Gly Phe Gly Arg Ile Gly Arg Asn
1               5              10              15

Tyr Phe Arg Ala Leu Leu Glu Gln Gly Ala Asp Ile Glu Ile Val Ala
         20            25              30

```
Val Asn Asp Leu Gly Asp Thr Ala Thr Ala His Leu Leu Lys Tyr
         35                  40                  45

Asp Thr Ile Leu Gly Arg Leu Lys Ala Glu Val Ser His Thr Glu Asp
 50                  55                  60

Thr Ile Thr Val Asp Gly Lys Thr Ile Lys Val Leu Ser Glu Arg Asn
 65                  70                  75                  80

Pro Ala Asp Ile Pro Trp Gly Leu Gly Val Asp Ile Val Glu
                 85                  90                  95

Ser Thr Gly Ile Phe Thr Lys Ala Asp Ala Glu Lys His Ile Ala
                100                 105                 110

Gly Gly Ala Lys Lys Val Leu Ile Ser Ala Pro Ala Lys Asp Glu Asp
         115                 120                 125

Ile Thr Ile Val Met Gly Val Asn Gln Asp Lys Tyr Asp Pro Ala Asn
         130                 135                 140

His His Val Ile Ser Asn Ala Ser Cys Thr Thr Asn Cys Val Ala Pro
145                 150                 155                 160

Met Ala Lys Val Leu Asp Glu Asn Phe Gly Ile Val Lys Gly Leu Met
                165                 170                 175

Thr Thr Val His Ala Tyr Thr Asn Asp Gln Arg Ile Leu Asp Phe Pro
                180                 185                 190

His Lys Asp Leu Arg Arg Ala Arg Ala Ala Glu Asn Ile Ile Pro
        195                 200                 205

Thr Thr Thr Gly Ala Ala Lys Ala Thr Ala Leu Val Leu Pro Gln Leu
        210                 215                 220

Lys Gly Lys Leu Asp Gly Ile Ala Met Arg Val Pro Val Pro Thr Gly
225                 230                 235                 240

Ser Ala Thr Asp Leu Val Glu Leu Gln Arg Glu Val Thr Lys Asp
                245                 250                 255

Glu Val Asn Ala Ala Phe Lys Lys Ala Ala Asp Asp Gly Asp Leu Lys
                260                 265                 270

Gly Ile Leu Phe Tyr Thr Glu Asp Ala Ile Val Ser Ser Asp Ile Thr
        275                 280                 285

Gly Asp Pro Ala Ser Cys Thr Phe Asp Ser Ser Leu Thr Met Val Gln
        290                 295                 300

Glu Gly Lys Ser Val Lys Ile Leu Gly Trp Tyr Asp Asn Glu Trp Gly
305                 310                 315                 320

Tyr Ser Asn Arg Leu Val Asp Leu Thr Val Phe Val Gly Asn Gln Leu
                325                 330                 335

<210> SEQ ID NO 47
<211> LENGTH: 335
<212> TYPE: PRT
<213> ORGANISM: Thermobifida fusca

<400> SEQUENCE: 47

Met Thr Ile Arg Val Gly Val Asn Gly Phe Gly Arg Ile Gly Arg Asn
1               5                   10                  15

Phe Trp Arg Ala Val Gln Ala Ala Gly Ser Asp Val Glu Ile Val
                20                  25                  30

Ala Val Asn Asp Leu Thr Asp Lys Ala Thr Leu Ala His Leu Leu Lys
         35                  40                  45

Tyr Asp Thr Val Leu Gly Thr Leu Pro Gly Glu Val Glu Val Gly Glu
 50                  55                  60

Asp Ser Ile Thr Val Gly Gly Thr Thr Met Lys Ala Leu Ala Gln Arg
```

-continued

```
                65                  70                  75                  80
Asp Pro Ala Gln Leu Pro Trp Gly Asp Leu Gly Val Asp Ile Val Val
                    85                  90                  95

Glu Ser Thr Gly Phe Phe Thr Lys Ala Glu Asp Ala Lys Lys His Leu
                100                 105                 110

Asp Ala Gly Ala Lys Lys Val Ile Ile Ser Ala Pro Ala Lys Gly Glu
            115                 120                 125

Asp Leu Thr Val Val Met Gly Val Asn Asp Asp Lys Tyr Asp Pro Ala
        130                 135                 140

Asn His His Ile Leu Ser Asn Ala Ser Cys Thr Thr Asn Cys Val Ala
145                 150                 155                 160

Pro Met Ala Lys Thr Leu Met Glu Asn Phe Gly Ile Val Lys Gly Leu
                165                 170                 175

Met Thr Thr Val His Ala Tyr Thr Asn Asp Gln Val Ile Leu Asp Tyr
                180                 185                 190

Pro His Lys Asp Leu Arg Arg Ala Arg Ala Ala Gln Asn Ile Ile
            195                 200                 205

Pro Thr Thr Thr Gly Ala Ala Lys Ala Thr Ala Leu Val Leu Pro Glu
        210                 215                 220

Leu Lys Gly Lys Leu Asp Gly Leu Ala Met Arg Val Pro Val Pro Asp
225                 230                 235                 240

Gly Ser Val Thr Asp Leu Val Val Thr Leu Glu Arg Glu Val Thr Lys
                245                 250                 255

Glu Glu Val Asn Ala Ala Phe Lys Ala Ala Glu Gly Ala Leu Lys
                260                 265                 270

Asp Ile Leu Val Tyr Thr Glu Asp Pro Ile Val Ser Ser Asp Ile Val
            275                 280                 285

Gly Thr Pro Ala Ser Cys Thr Phe Asp Ala Ser Leu Thr Met Ala Phe
        290                 295                 300

Gly Thr Gln Val Lys Val Gly Trp Tyr Asp Asn Glu Trp Gly Tyr
305                 310                 315                 320

Ser Asn Arg Leu Val Asp Leu Val Lys Leu Val Gly Ser Asn Leu
                325                 330                 335
```

<210> SEQ ID NO 48
<211> LENGTH: 335
<212> TYPE: PRT
<213> ORGANISM: Bacillus halodurans

<400> SEQUENCE: 48

```
Met Ala Thr Lys Ile Gly Ile Asn Gly Phe Gly Arg Ile Gly Arg Asn
1               5                   10                  15

Val Phe Arg Ala Ala Leu Asn Asn Pro Asn Val Glu Val Val Ala Ile
                20                  25                  30

Asn Asp Leu Thr Asp Ala Asn Met Leu Ala His Leu Leu Lys Tyr Asp
            35                  40                  45

Ser Val His Gly Lys Leu Asp Ala Glu Val Lys Val Asp Gly Asp Ser
        50                  55                  60

Leu Val Val Asn Gly His Ser Val Lys Val Lys Ala Glu Arg Asp Pro
65                  70                  75                  80

Ala Gln Leu Gly Trp Gly Asp Leu Gly Val Glu Val Val Glu Ser
                85                  90                  95

Thr Gly Arg Phe Thr Asn Arg Glu Asp Ala Ala Lys His Leu Glu Ala
                100                 105                 110
```

```
Gly Ala Lys Lys Val Ile Ile Ser Ala Pro Ala Lys Asp Glu Asp Ile
            115                 120                 125

Thr Val Val Met Gly Val Asn Glu Asn Lys Tyr Asp Pro Ala Asn His
        130                 135                 140

His Val Leu Ser Asn Ala Ser Cys Thr Thr Asn Cys Leu Ala Pro Phe
145                 150                 155                 160

Ala Lys Val Leu Asn Asp Lys Phe Gly Ile Arg Arg Gly Met Met Thr
                165                 170                 175

Thr Val His Ser Tyr Thr Asn Asp Gln Gln Ile Leu Asp Leu Pro His
            180                 185                 190

Lys Asp Tyr Arg Arg Ala Arg Ala Ala Glu Asn Ile Ile Pro Thr
        195                 200                 205

Thr Thr Gly Ala Ala Lys Ala Val Ala Leu Val Leu Pro Glu Leu Lys
        210                 215                 220

Gly Lys Leu Asn Gly Gly Ala Met Arg Val Pro Thr Pro Asn Val Ser
225                 230                 235                 240

Leu Val Asp Leu Val Ala Glu Leu Asp Lys Glu Val Thr Ala Glu Glu
                245                 250                 255

Val Asn Ala Ala Leu Lys Glu Ala Ala Glu Gly Asp Leu Lys Gly Ile
            260                 265                 270

Leu Ala Tyr Ser Glu Glu Pro Leu Val Ser Gly Asp Tyr Asn Gly Asn
        275                 280                 285

Pro Ala Ser Ser Thr Ile Asp Ala Leu Ser Thr Met Val Met Glu Gly
        290                 295                 300

Asn Met Val Lys Val Ile Ser Trp Tyr Asp Asn Glu Ser Gly Tyr Ser
305                 310                 315                 320

His Arg Val Val Asp Leu Val Asp Tyr Ile Ala Lys Gln Gly Leu
                325                 330                 335

<210> SEQ ID NO 49
<211> LENGTH: 334
<212> TYPE: PRT
<213> ORGANISM: Corynebacterium diphtheriae

<400> SEQUENCE:

Met Ala Lys Val Leu Asp Glu Lys Phe Gly Ile Val Lys Gly Leu Met
                165                 170                 175

Thr Thr Ile His Ala Tyr Thr Gly Asp Gln Arg Leu His Asp Ala Pro
            180                 185                 190

His Arg Asp Leu Arg Arg Ala Arg Ala Ala Gln Asn Ile Val Pro
        195                 200                 205

Thr Ser Thr Gly Ala Ala Lys Ala Val Ala Leu Val Leu Pro Glu Leu
    210                 215                 220

Lys Gly Lys Leu Asp Gly Phe Ala Met Arg Val Pro Val Ile Thr Gly
225                 230                 235                 240

Ser Ala Thr Asp Leu Thr Phe Glu Thr Thr Lys Glu Val Ser Ala Glu
                245                 250                 255

Glu Ile Asn Ala Ala Met Lys Glu Ala Ala Gly Glu Leu Lys Gly
            260                 265                 270

Val Leu Ala Tyr Thr Glu Asp Pro Ile Val Ser Thr Asp Ile Val Thr
        275                 280                 285

Asp Ala His Ala Ser Ile Phe Asp Ala Gly Leu Thr Lys Val Ile Gly
    290                 295                 300

Asn Gln Val Lys Val Val Ser Trp Tyr Asp Asn Glu Trp Gly Tyr Ser
305                 310                 315                 320

Asn Gln Leu Val Ser Leu Thr Glu Tyr Val Gly Glu Arg Leu
                325                 330

<210> SEQ ID NO 50
<211> LENGTH: 1008
<212> TYPE: DNA
<213> ORGANISM: Streptomyces clavuligerus

<400> SEQUENCE: 50
gtgacgatcc gcgtaggcat caacggcttt ggccgcatcg gtcgtaacta cttccgcgcg     60
ctgctggagc agggtgcaga catcgagatc gtggctgtca acgacctggg tgacaccgcg    120
accacggctc acctgctgaa gtacgacacc attctgggac gcctcaaggc cgaggtcacc    180
cacaccgccg acaccatcac cgtcgacggc cacacgatca aggtgctctc cgagcgcaac    240
cccgccgaca tcccgtgggg cgagctgggc gtcgacatcg tgatcgagtc gacgggcatc    300
ttcaccaaga aggccgacgc cgagaagcac ctcgccggcg gcgccaagaa ggtcctgatc    360
tcggctccgg ccaaggacga ggacatcacc ctggtgatgg gtgtcaacca ggacacctac    420
gacccggcgc agcaccacgt catctccaac gcctcctgca ccaccaactg tgtggcgccg    480
atggcgaagg tgctcgacga gaacttcggc atcgtccgcg gtctgatgac gacggtccac    540
gcctacacca cgaccagcg catcctggac ttcccgcact cggacctgcg ccgcgcccgc    600
gccgccgcgg agaacatcat cccgaccacc acgggtgccg ccaaggccac cgcgctggtc    660
ctcccgcagc tcaagggcaa gctggacggc atcgccatgc gcgtcccggt ccccaccggc    720
tccgcgaccg acctggtcgt cgagctgagc cgcgaggtca ccaaggacga ggtcaacgcc    780
gcgttcaaga aggccgccga gggcgagctc cagggcatcc tgagctacac cgaggacccg    840
atcgtctcct cggacatcgt cggcgacccg gcctcctgca ccttcgactc ctccctgacc    900
atggtccagg agggcaactc ggtgaagatc ctcggctggt acgacaacga gtggggctac    960
tccaaccgcc tcgtcgacct cacggtcttc gtcggcgagc agctctga              1008

<210> SEQ ID NO 51
<211> LENGTH: 25

```
<212> TYPE: DNA
<213> ORGANISM: Artificial
<220> FEATURE:
<223> OTHER INFORMATION: Synthetic oligonucleotide primer

<400> SEQUENCE: 51
cacgcctcct gtaccaccaa ctgtg                                           25

<210> SEQ ID NO 52
<211> LENGTH: 26
<212> TYPE: DNA
<213> ORGANISM: Artificial
<220> FEATURE:
<223> OTHER INFORMATION: Syntheitic oligonucleotide primer

<400> SEQUENCE: 52
tggagtagcc ccactcgttt catacc                                          26

<210> SEQ ID NO 53
<211> LENGTH: 1446
<212> TYPE: DNA
<213> ORGANISM: Streptomyces clavuligerus

<400> SEQUENCE: 53
gtgactgtca atgaggactc gttcaccaac tggaagaacc gcgaggagat cgcggagtcg      60
atgatcccgg tcatcggcaa gctccaccgg gagcgggacg tcacgatcct gctccacagc     120
cgttccctgg tgaacaagtc ggtggtcagc atcctcaaga cccaccgttt cgctcgccag     180
atcgccggcg aggagctgtc cgtcaccgag acgctgccct tcctcaagac cctcgccgcc     240
ctggatctcg gccccctccca gatcgacctg gcatgctcg ccgcgaccta ccgggcggac     300
gaccgcggtc tgacggtgga ggagttcacc gccgaggccg tcgccggtgc cacgggtgcc     360
aacaagatcg agcgccgcga gggacgcgat gtcgtcctct acgggttcgg ccgcatcggc     420
cgtctcctcg cccgcctgct catcgagaag gccggctccg gcaacgggct gcgcctgcgc     480
gccatcgtcg tccgcaaggg cgcgggccag gacctcgtca agcgcgcctc gctgctccgc     540
cgtgactcga tccacggcca gttccacggc acgatcaccg tggacgagga gaacagcacc     600
atcgtcgcca acggcaacga gatcaaggtg atctactcgg acgacccgac ggcggtggac     660
tacaccgcgt acggcatccg ggacgccatc ctcatcgaca acaccggccg ctggcgcgac     720
cgcgagggcc tgtcgaagca tctgcgcccc ggtatcgcca aggtggtcct gaccgccccg     780
ggcaagggcc acgtccccaa catcgtccac ggcgtcaacc acgacacgat caagccggac     840
gagcagatcc tgtcctgcgc ctcctgcacc accaacgcga tcgtcccgcc gctgaaggcg     900
atggcggacg agttcggtgt cctcggcggc catgtggaga cggtccactc gtacacgaac     960
gaccagaacc tgctggacaa ctaccacaag tccgaccgcc gtggccgctc ggccgcgctc    1020
aatatggtga tcaccgagac cggtgccgcc tccgccgtgg ccaaggcgct gcccgacctc    1080
aaggcgaaga tcaccggaag ctccatccgg gtgccggtgc cggatgtctc gatcgcgatc    1140
ctcagcctgc ggctcgggcg cgagaccacc cgtgaggaag tcctcgacca tctgcgtgag    1200
gtgtcgctga cctcgccgct caagcgccag atcgacttca tcacggcgcc cgacgcggtg    1260
tcgaacgact tcgtcggctc gcgccacgcc tccatcgtgg acgccggagc caccaaggtc    1320
gagggcgaca acgcgatcct gtacctgtgg tacgacaacg agttcggcta ctcctgccag    1380
gtcgtccgcg tggtccagca cgtctccggg gtggagtacc cgaccttccc ggcgccggtc    1440
gcctga                                                              1446
```

<210> SEQ ID NO 54
<211> LENGTH: 1684
<212> TYPE: DNA
<213> ORGANISM: Artificial
<220> FEATURE:
<223> OTHER INFORMATION: DNA sequence of the PCR product of the
gap1::tsr region in gap1 mutant

<400> SEQUENCE: 54

| | | | | | |
|---|---|---|---|---|---|
| tccccgcggt | ggcggccgct | ctagaactag | tggatccccc | attcatctcc | aacgcctcct | 60 |
| gtaccaccaa | ctgtgtggcg | ccgatggcga | aggtgctcga | cgagaacttc | ggcatcgtcc | 120 |
| gcggtctgaa | tgacgacggt | ccacgcctac | accaacgacc | agcgcatcct | ggacttcccg | 180 |
| cactcggacc | tgcgccgcgc | ccgcgccgcc | gcggagaaca | tcatcccgac | caccacgggt | 240 |
| gccgccaagg | ccaccgcgct | ggtcctcccg | cagctcaagg | gcaagctgga | cggcatcgcc | 300 |
| atgcgcgtcc | cggtccccac | cggctccgcg | accgacctgg | tcgtcgagct | gwgatcaagg | 360 |
| cgaatacttc | atatgsgggg | atcgaccgcg | cgggtcccgg | acggggaaga | gcggggagct | 420 |
| ttgccagaga | gcgacgactt | ccccttgcgt | tggtgattgc | cggtcagggc | agccatccgc | 480 |
| catcgtcgcs | tagggtgtca | cacccccagga | atcgcgtcac | tgaacacagc | agccggtagg | 540 |
| acgaccatga | ctgagttgga | caccatcgca | atccgtccg | atcccgcggt | gcagcggatc | 600 |
| atcgatgtca | ccaagccgts | gcgatccaac | ataaagacaa | cgttgatcga | ggacgtcgag | 660 |
| cccctcatgc | acagcatcgc | ggccggggtg | gagttcatcg | aggtctacgg | cagcgacagc | 720 |
| agtcctttc | catctgagtt | gctggatctg | tgcgggcggc | agaacatacc | ggtccgcctc | 780 |
| atcgactcct | cgatcgtcaa | ccagttgttc | aaggggagc | ggaaggscaa | gacattcggc | 840 |
| atcgcccgcg | tccctcgccc | ggccaggttc | ggcgatatcg | cgagccggcg | tggggacgtc | 900 |
| gtcgttctcg | acggggtgaa | gatcgtcggg | aacatcggcg | cgatagtacg | cacgtcgctc | 960 |
| gcgctcggag | cgtcggggat | catcctggtc | gacagtgaca | tcaccagcat | cgcggaccgg | 1020 |
| cgtctccaaa | gggccagccg | aggttacgtc | ttctcccttc | ccgtcgttct | ctccgstcgc | 1080 |
| gaggaggcca | tcgccttcat | tcgggacagc | ggtatgcagc | tgatgacgct | caaggcggat | 1140 |
| ggcgacattt | ccgtgaagga | actcggggac | aatccggatc | ggctggcctt | gctgttcggc | 1200 |
| agcgaaaagg | gtgggccttc | cgacctgttc | gaggaggcgt | cttccgcctc | ggtttccatc | 1260 |
| cccatgatga | gccagaccga | gtctctcaac | gtttccgttt | ccctcggaat | cgcgctgcac | 1320 |
| gagaggatcg | acaggaatct | cgcggccaac | cgataagcgc | ctctgttcct | cggacgctcg | 1380 |
| gttcctcgac | ctcgattcgt | cagtgatgat | ctgagccgcg | aggtcaccaa | ggacgaggtc | 1440 |
| aacgccgcgt | tcaagaaggc | cgccgagggc | gagctccagg | gcatcctgag | ctacaccgag | 1500 |
| gacccgatcg | tctcctcgga | catcgtcggc | gacccggcct | cctgcacctt | cgactcctcc | 1560 |
| ctgaccatgg | tccaggaggg | caactcggtg | aagatcctcg | gctggtatga | aacgagtggg | 1620 |
| gctactccag | ggctgcagga | attcgatatc | aagcttatcg | ataccgtcga | cctcgaggag | 1680 |
| gggc | | | | | | 1684 |

<210> SEQ ID NO 55
<211> LENGTH: 2922
<212> TYPE: DNA
<213> ORGANISM: Artificial
<220> FEATURE:
<223> OTHER INFORMATION: DNA seuqnece of the PCR product of teh
gap::2apr region in gap2 mutant

<400> SEQUENCE: 55

-continued

```
gtgactgtca atgaggactc gttcaccaac tggaagaacc gcgaggagat cgcggagtcg      60
atgatcccgg tcatcggcaa gctccaccgg gagcgggacg tcacgatcct gctccacagc    120
cgttccctgg tgaacaagtc ggtggtcagc atcctcaaga cccaccgttt cgctcgccag    180
atcgccggcg aggagctgtc cgtcaccgag acgctgccct tcctcaagac cctcgccgcc    240
ctggatctcg gcccctccca gatcgacctg ggcatgctcg ccgcgaccta ccgggcggac    300
gaccgcggtc tgacggtgga ggagttcacc gccgaggccg tcgccggtgc cacgggtgcc    360
aacaagatcg agcgccgcga gggacgcgat gtcgtcctct acgggttcgg ccgcatcggc    420
cgtctcctcg cccgcctgct catcgagaag gccggctccg gcaacgggct cgcctgcgc    480 gccatcgtcg tccgcaaggg cgcgggccag gacctcgtca gcgcgcctc gctgctccgc    540 cgtgactcga tccacggcca gttccacggc acgatcaccg tggacgagga gaacagcacc    600
atcgtcgcca acggcaacga gatcaaggtg atctactcgg acgacccgac ggcggtggac    660
tacaccgcgt acggcatccg ggacgccatc ctcatcgaca acaccggccg ctggcgcgac    720
cgcgagggcc tgtcgaagca tctgcgcccc ggtatcgcca aggtggtcct gaccgccccg    780
ggcaagggcg acgtccccaa catcgtccac ggcgtcaacc gcacacgat caagccggac    840 gagcagatcc tgtcctgcgc ctcctgcacc accaacgcga tcgtcccgcc gctgaaggcg    900
atggcggacg agttcggtgt cctcggcggc catgtggaga cggtccactc gtacacgaac    960
gaccagaacc tgctggacaa ctaccacaag tccgaccgcc gtggccgctc ggccgcgctc   1020
aatatggtga tcaccgagac cggtgccgcc tccgccgtgg ccaaggcgct gcccgacctc   1080
aaggcgaaga tcaccggaag ctccatccgg gtgccggtgc cggatgtctc gatcgaattc   1140
agatgctcac ggtaactgat gccgtatttg cagtaccagc gtacggccca cagaatgatg   1200
tcacgctgaa aatgccggcc tttgaatggg ttcatgtgca gctccatcag caaaagggga   1260
tgataagttt atcaccaccg actatttgca acagtgccgt tgatcgtgct atgatcgact   1320
gatgtcatca gcggtggagt gcaatgtcgt gcaatacgaa tggcgaaaag ccgagctcat   1380
cggtcagctt ctcaaccttg gggttacccc cggcggtgtg ctgctggtcc acagctcctt   1440
ccgtagcgtc cggcccctcg aagatgggcc acttggactg atcgaggccc tgcgtgctgc   1500
gctgggtccg ggagggacgc tcgtcatgcc ctcgtggtca ggtctggacg acgagccgtt   1560
cgatcctgcc acgtcgcccg ttacaccgga ccttggagtt gtctctgaca cattctggcg   1620
cctgccaaat gtaaagcgca gcgcccatcc atttgccttt gcggcagcgg ggccacaggc   1680
agagcagatc atctctgatc cattgcccct gccacctcac tcgcctgcaa gcccggtcgc   1740
ccgtgtccat gaactcgatg ggcaggtact tctcctcggc gtgggacacg atgccaacac   1800
gacgctgcat cttgccgagt tgatggcaaa ggttccctat ggggtgccga cactgcac   1860 cattcttcag gatggcaagt tggtacgcgt cgattatctc gagaatgacc actgctgtga   1920
gcgctttgcc ttggcggaca ggtggctcaa ggagaagagc cttcagaagg aaggtccagt   1980
cggtcatgcc tttgctcggt tgatccgctc ccgcgacatt gtggcgacag ccctgggtca   2040
actgggccga gatccgttga tcttcctgca tccgccagag gcgggatgcg aagaatgcga   2100
tgccgctcgc cagtcgattg gctgagctca tgagcggaga acgagatgac gttgaggggg   2160
caaggtcgcg ctgattgctg gggcaacacg tggagcggat cggggattgt ctttcttcag   2220
ctcgctgatg atatgctgac gctcaatgcc gtttggcctc cgactaacga aaatcccgca   2280
tttggacggc tgatccgatt ggcacggcgg acggcgaatg gcggagcaga cgctcgtccg   2340
```

-continued

```
ggggcaatga gatatgaaaa agcctgaact caccgcgacg tctgtcgaga agtttctgat    2400
cgaaaagttc gacagcgtct ccgacctgat gcagctctcg gagggcgaag aatctcgtgc    2460
tttcagcttc gatgtaggag ggcgtggata tgtcctgcgg gtaaatagct gcgccgatgg    2520
tttctacaaa gatcgttatg tttatcggca ctttgcatcg gccgcgctcc cgattccgga    2580
agtgcttgac attggggaat tatcacgaat tcgatcctca gcctgcggct cgggcgcgag    2640 accaccgtg aggaagtcct cgaccatctg cgtgaggtgt cgctgacctc gccgctcaag    2700
cgccagatcg acttcatcac ggcgcccgac gcggtgtcga acgacttcgt cggctcgcgc    2760
cacgcctcca tcgtggacgc cggagccacc aaggtcgagg cgacaacgc gatcctgtac    2820 ctgtggtacg acaacgagtt cggctactcc tgccaggtcg tccgcgtggt ccagcacgtc    2880
tccggggtgg agtacccgac cttcccggcg ccggtcgcct ga                      2922
```

<210> SEQ ID NO 56
<211> LENGTH: 481
<212> TYPE: PRT
<213> ORGANISM: Streptomyces clavuligerus

<400> SEQUENCE: 56

```
Met Thr Val Asn Glu Asp Ser Phe Thr Asn Trp Lys Asn Arg Glu Glu
1               5                   10                  15

Ile Ala Glu Ser Met Ile Pro Val Ile Gly Lys Leu His Arg Glu Arg
            20                  25                  30

Asp Val Thr Ile Leu Leu His Ser Arg Ser Leu Val Asn Lys Ser Val
        35                  40                  45

Val Ser Ile Leu Lys Thr His Arg Phe Ala Arg Gln Ile Ala Gly Glu
    50                  55                  60

Glu Leu Ser Val Thr Glu Thr Leu Pro Phe Leu Lys Thr Leu Ala Ala
65                  70                  75                  80

Leu Asp Leu Gly Pro Ser Gln Ile Asp Leu Gly Met Leu Ala Ala Thr
                85                  90                  95

Tyr Arg Ala Asp Asp Arg Gly Leu Thr Val Glu Glu Phe Thr Ala Glu
            100                 105                 110

Ala Val Ala Gly Ala Thr Gly Ala Asn Lys Ile Glu Arg Arg Glu Gly
        115                 120                 125

Arg Asp Val Val Leu Tyr Gly Phe Gly Arg Ile Gly Arg Leu Leu Ala
    130                 135                 140

Arg Leu Leu Ile Glu Lys Ala Gly Ser Gly Asn Gly Leu Arg Leu Arg
145                 150                 155                 160

Ala Ile Val Val Arg Lys Gly Ala Gly Gln Asp Leu Val Lys Arg Ala
                165                 170                 175

Ser Leu Leu Arg Arg Asp Ser Ile His Gly Gln Phe His Gly Thr Ile
            180                 185                 190

Thr Val Asp Glu Glu Asn Ser Thr Ile Val Ala Asn Gly Asn Glu Ile
        195                 200                 205

Lys Val Ile Tyr Ser Asp Asp Pro Thr Ala Val Asp Tyr Thr Ala Tyr
    210                 215                 220

Gly Ile Arg Asp Ala Ile Leu Ile Asp Asn Thr Gly Arg Trp Arg Asp
225                 230                 235                 240

Arg Glu Gly Leu Ser Lys His Leu Arg Pro Gly Ile Ala Lys Val Val
                245                 250                 255

Leu Thr Ala Pro Gly Lys Gly Asp Val Pro Asn Ile Val His Gly Val
            260                 265                 270
```

```
Asn His Asp Thr Ile Lys Pro Asp Glu Gln Ile Leu Ser Cys Ala Ser
        275                 280                 285

Cys Thr Thr Asn Ala Ile Val Pro Pro Leu Lys Ala Met Ala Asp Glu
        290                 295                 300

Phe Gly Val Leu Gly Gly His Val Glu Thr Val His Ser Tyr Thr Asn
305                 310                 315                 320

Asp Gln Asn Leu Leu Asp Asn Tyr His Lys Ser Asp Arg Arg Gly Arg
                325                 330                 335

Ser Ala Ala Leu Asn Met Val Ile Thr Glu Thr Gly Ala Ala Ser Ala
        340                 345                 350

Val Ala Lys Ala Leu Pro Asp Leu Lys Ala Lys Ile Thr Gly Ser Ser
        355                 360                 365

Ile Arg Val Pro Val Pro Asp Val Ser Ile Ala Ile Leu Ser Leu Arg
        370                 375                 380

Leu Gly Arg Glu Thr Thr Arg Glu Glu Val Leu Asp His Leu Arg Glu
385                 390                 395                 400

Val Ser Leu Thr Ser Pro Leu Lys Arg Gln Ile Asp Phe Ile Thr Ala
                405                 410                 415

Pro Asp Ala Val Ser Asn Asp Phe Val Gly Ser Arg His Ala Ser Ile
                420                 425                 430

Val Asp Ala Gly Ala Thr Lys Val Glu Gly Asp Asn Ala Ile Leu Tyr
        435                 440                 445

Leu Trp Tyr Asp Asn Glu Phe Gly Tyr Ser Cys Gln Val Val Arg Val
        450                 455                 460

Val Gln His Val Ser Gly Val Glu Tyr Pro Thr Phe Pro Ala Pro Val
465                 470                 475                 480

Ala

<210> SEQ ID NO 57
<211> LENGTH: 11
<212> TYPE: PRT
<213> ORGANISM: Artificial
<220> FEATURE:
<223> OTHER INFORMATION: Amino acid sequence variants of motif M1
<220> FEATURE:
<221> NAME/KEY: MISC_FEATURE
<222> LOCATION: (1)..(1)
<223> OTHER INFORMATION: x is H or Q
<220> FEATURE:
<221> NAME/KEY: MISC_FEATURE
<222> LOCATION: (2)..(2)
<223> OTHER INFORMATION: x is H, T or N
<220> FEATURE:
<221> NAME/KEY: MISC_FEATURE
<222> LOCATION: (3)..(3)
<223> OTHER INFORMATION: x is V or I

<400> SEQUENCE: 57

Xaa Xaa Xaa Ser Asn Ala Ser Cys Thr Thr Asn
1               5                   10

<210> SEQ ID NO 58
<211> LENGTH: 10
<212> TYPE: PRT
<213> ORGANISM: Artificial
<220> FEATURE:
<223> OTHER INFORMATION: Sequence variants of motif M2
<220> FEATURE:
<221> NAME/KEY: MISC_FEATURE
<222> LOCATION: (1)..(1)
<223> OTHER INFORMATION: x is S, K or R
<220> FEATURE:
<221> NAME/KEY: MISC_FEATURE
```

```
<222> LOCATION: (3)..(3)
<223> OTHER INFORMATION: x is L or Y

<400> SEQUENCE: 58

Xaa Asp Xaa Arg Arg Ala Arg Ala Ala Ala
1               5                   10

<210> SEQ ID NO 59
<211> LENGTH: 10
<212> TYPE: PRT
<213> ORGANISM: Artificial
<220> FEATURE:
<223> OTHER INFORMATION: Sequence variants of motif M3
<220> FEATURE:
<221> NAME/KEY: MISC_FEATURE
<222> LOCATION: (6)..(6)
<223> OTHER INFORMATION: x is S, W or T
<220> FEATURE:
<221> NAME/KEY: MISC_FEATURE
<222> LOCATION: (8)..(8)
<223> OTHER INFORMATION: x is Y or F
<220> FEATURE:
<221> NAME/KEY: MISC_FEATURE
<222> LOCATION: (10)..(10)
<223> OTHER INFORMATION: x is H, A, or T

<400> SEQUENCE: 59

Trp Tyr Asp Asn Glu Xaa Gly Xaa Ser Xaa
1               5                   10
```